United States Patent
Whitaker et al.

(10) Patent No.: US 10,905,443 B2
(45) Date of Patent: Feb. 2, 2021

(54) BONE PLATE FASTENING SYSTEM

(71) Applicant: DePuy Synthes Products, Inc., Raynham, MA (US)

(72) Inventors: Weston Whitaker, Glenmoore, PA (US); Joseph Capozzoli, Mount Laurel, NJ (US); Raymond Schmitt, Havertown, PA (US); Peter Fatone, Exton, PA (US); Michael Brace, Lansdale, PA (US); Eric Lui, Royersford, PA (US); Benjamin Barrall, Lititz, PA (US); Kenny Koay, West Chester, PA (US); Steven Opsitnick, Newark, DE (US)

(73) Assignee: DePuy Synthes Products, Inc., Raynham, MA (US)

( * ) Notice: Subject to any disclaimer, the term of this patent is extended or adjusted under 35 U.S.C. 154(b) by 241 days.

(21) Appl. No.: 15/848,753

(22) Filed: Dec. 20, 2017

(65) Prior Publication Data

US 2018/0177510 A1 Jun. 28, 2018

Related U.S. Application Data

(60) Provisional application No. 62/439,311, filed on Dec. 27, 2016, provisional application No. 62/516,402, filed on Jun. 7, 2017.

(51) Int. Cl.
*A61B 17/70* (2006.01)
*A61B 17/80* (2006.01)
(Continued)

(52) U.S. Cl.
CPC ...... *A61B 17/1728* (2013.01); *A61B 17/8057* (2013.01); *A61B 17/686* (2013.01);
(Continued)

(58) Field of Classification Search
CPC .......................... A61B 17/1728; A61B 17/808
See application file for complete search history.

(56) References Cited

U.S. PATENT DOCUMENTS 6,379,364 B1 * 4/2002 Brace ................. A61B 17/1728
606/86 R
2007/0167953 A1 7/2007 Prien et al.
(Continued)

FOREIGN PATENT DOCUMENTS

WO 2009/121144 A1 10/2009
WO 2010/107692 A1 9/2010

*Primary Examiner* — Nicholas W Woodall
(74) *Attorney, Agent, or Firm* — BakerHostetler

(57) ABSTRACT

A screw guide includes a first end, a second end spaced from the first end, a guide body that extends from the first end to the second end, and a guide hole that extends through the guide body. The guide body includes a first guide surface and a second guide surface, the first guide surface defines a first opening of the guide hole, and the second guide surface is spaced from the first guide surface in a first guide direction. The second guide surface defines a second opening of the guide hole, the guide body includes a leg portion that extends from the second guide surface in the first guide direction such that the leg portion is spaced from the second opening in a second guide direction that is perpendicular to the first guide direction.

18 Claims, 18 Drawing Sheets

(51) Int. Cl.
  *A61B 17/17*  (2006.01)
  *A61B 17/68*  (2006.01)
  *A61B 17/84*  (2006.01)

(52) U.S. Cl.
  CPC ....... *A61B 17/8047* (2013.01); *A61B 17/8061* (2013.01); *A61B 17/8085* (2013.01); *A61B 17/84* (2013.01)

(56) References Cited

U.S. PATENT DOCUMENTS

| | | |
|---|---|---|
| 2011/0004254 A1 | 1/2011 | Beger et al. |
| 2015/0201975 A1 | 7/2015 | Paul |
| 2016/0051297 A1* | 2/2016 | Steffensmeier ...... A61B 17/808 606/86 B |

* cited by examiner

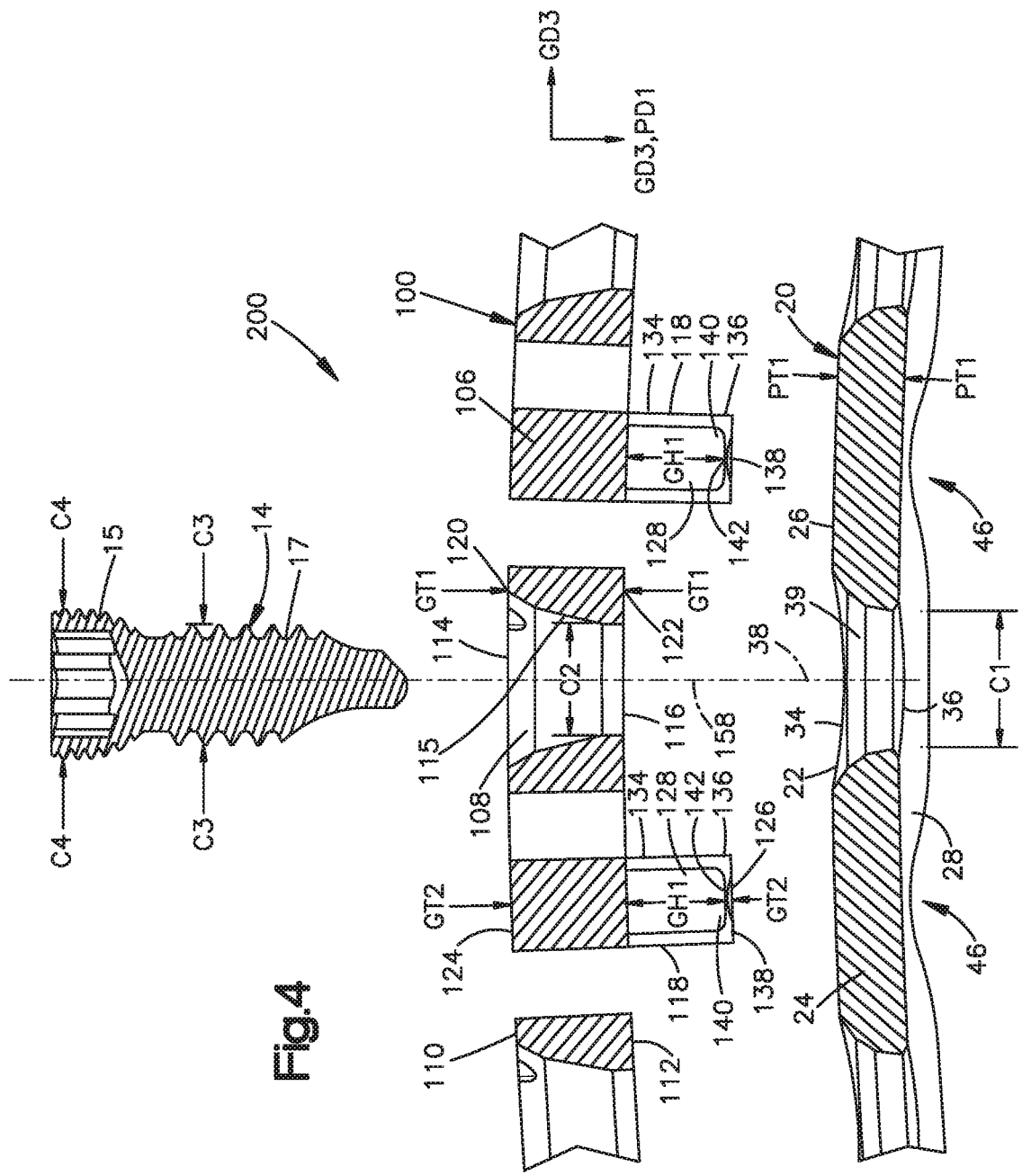

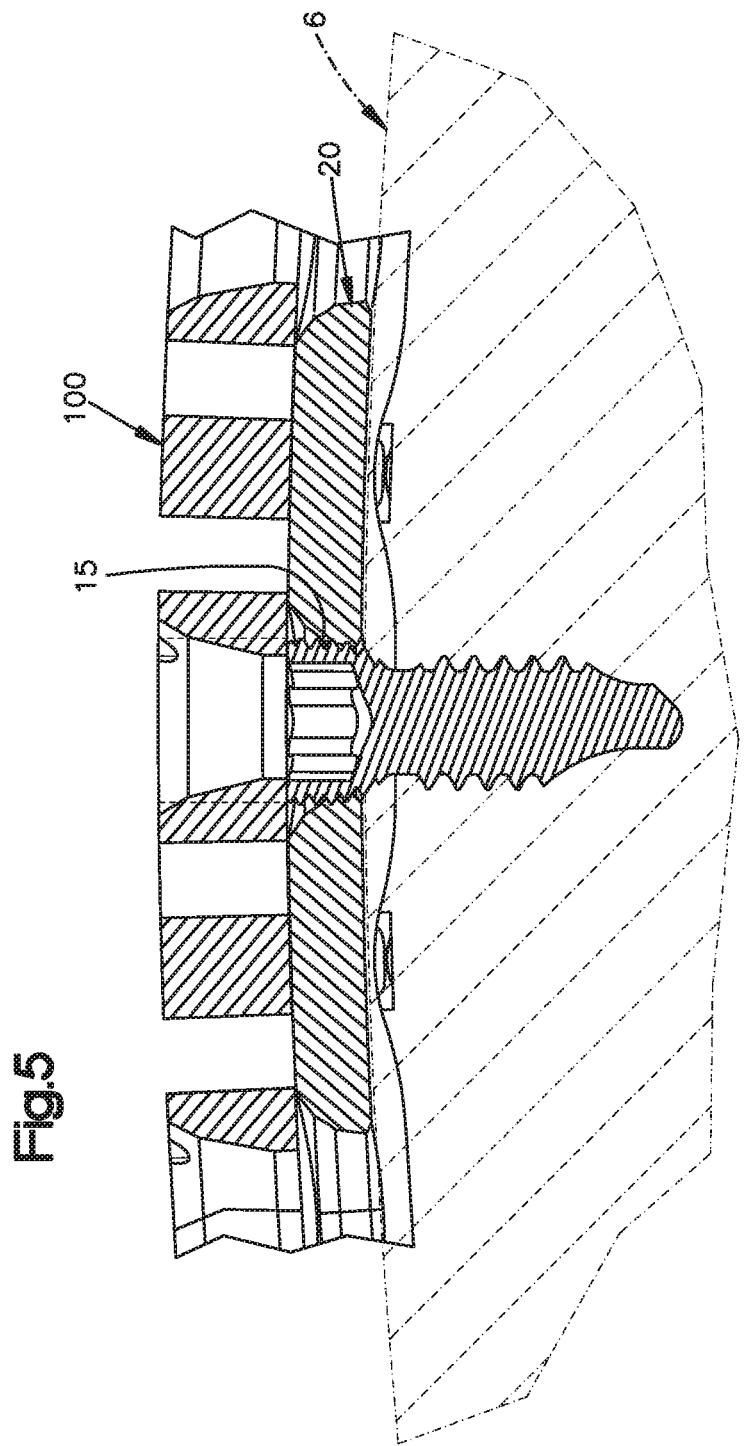

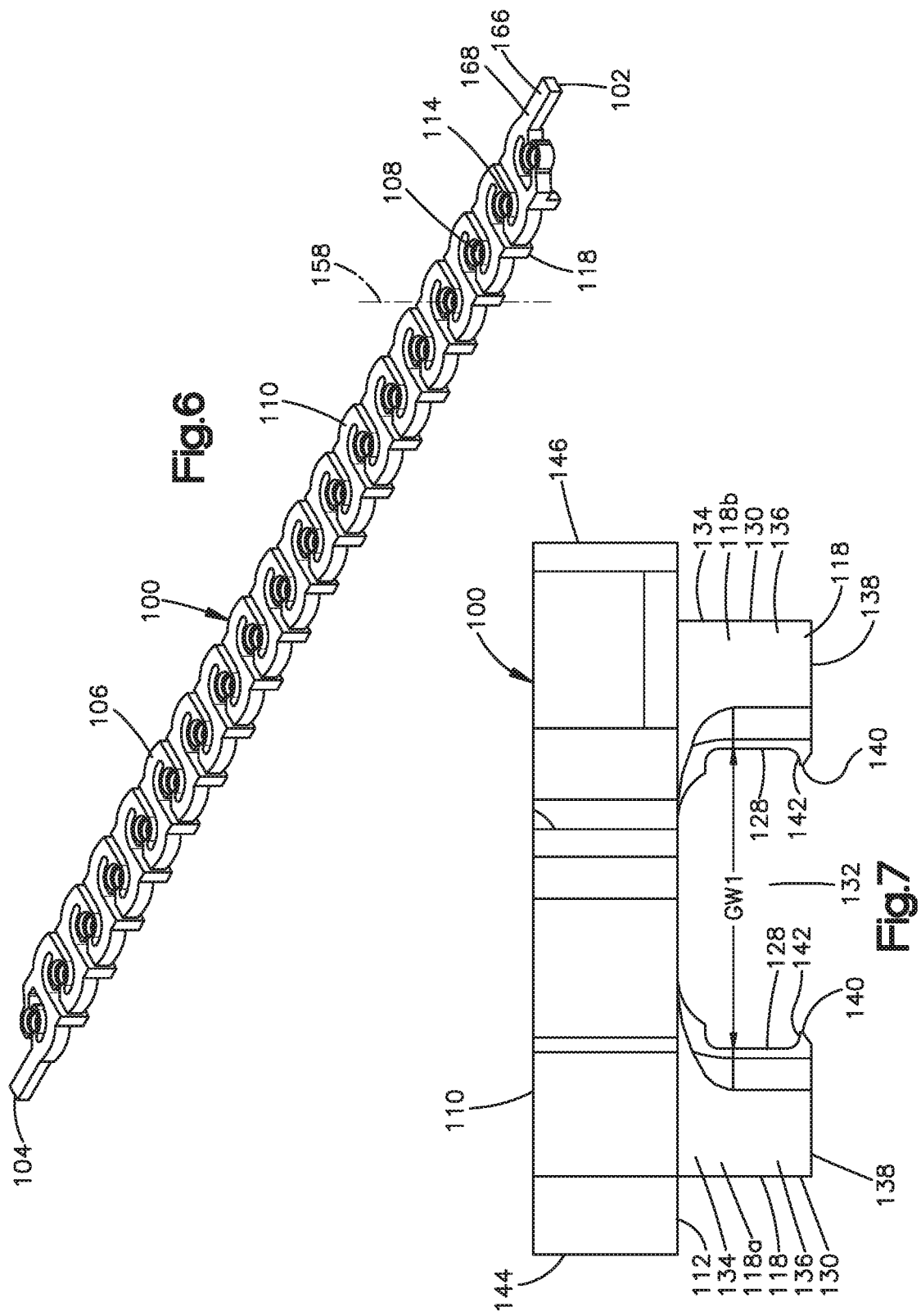

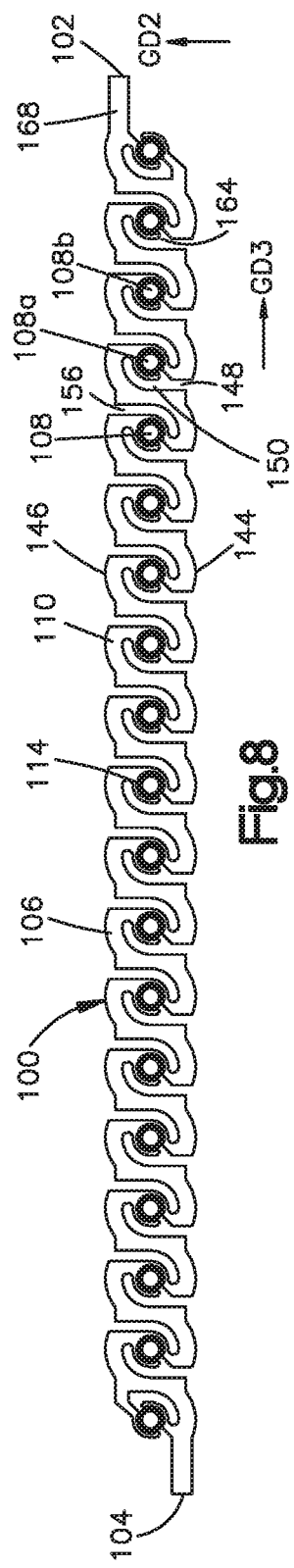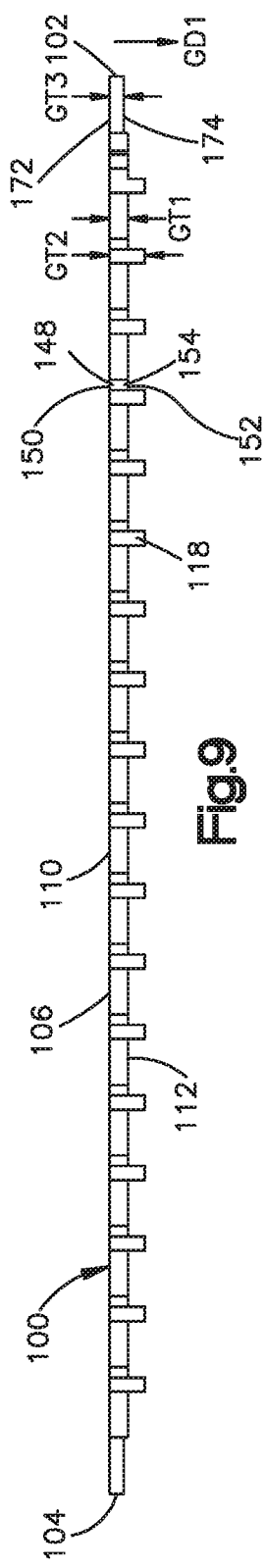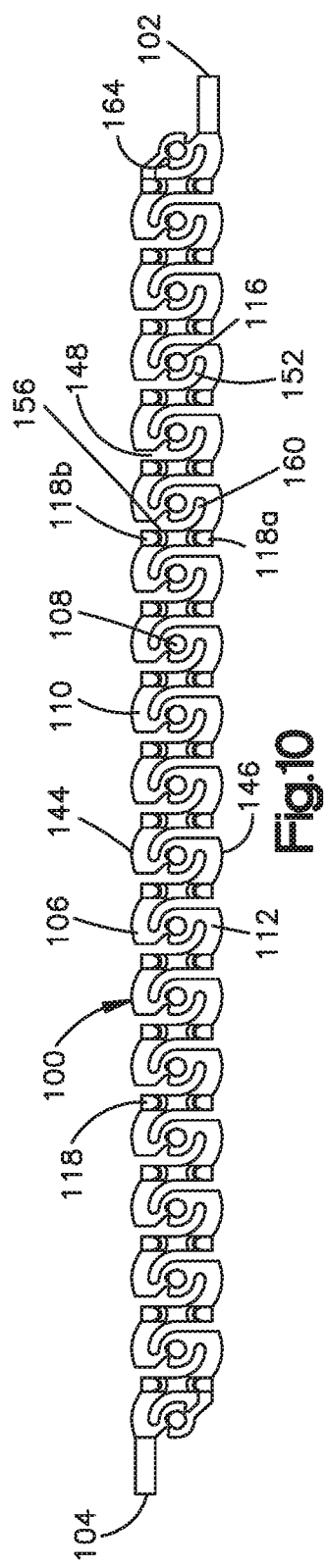

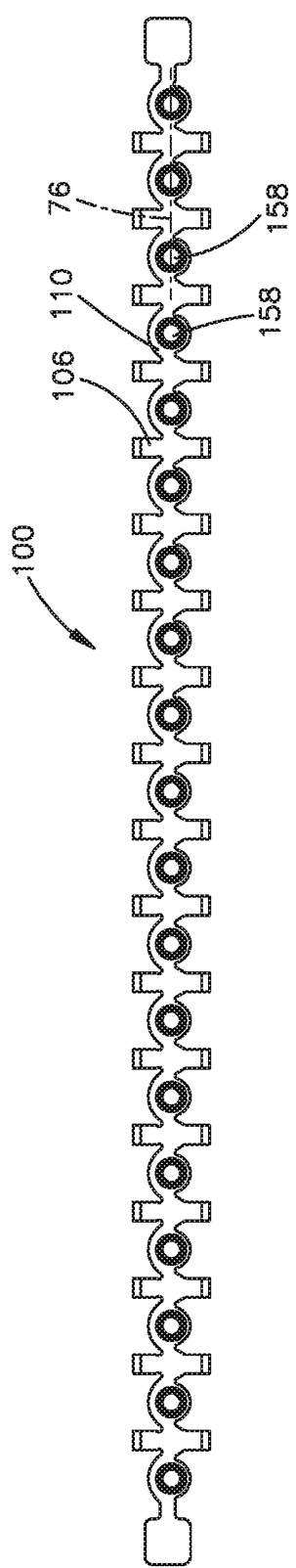

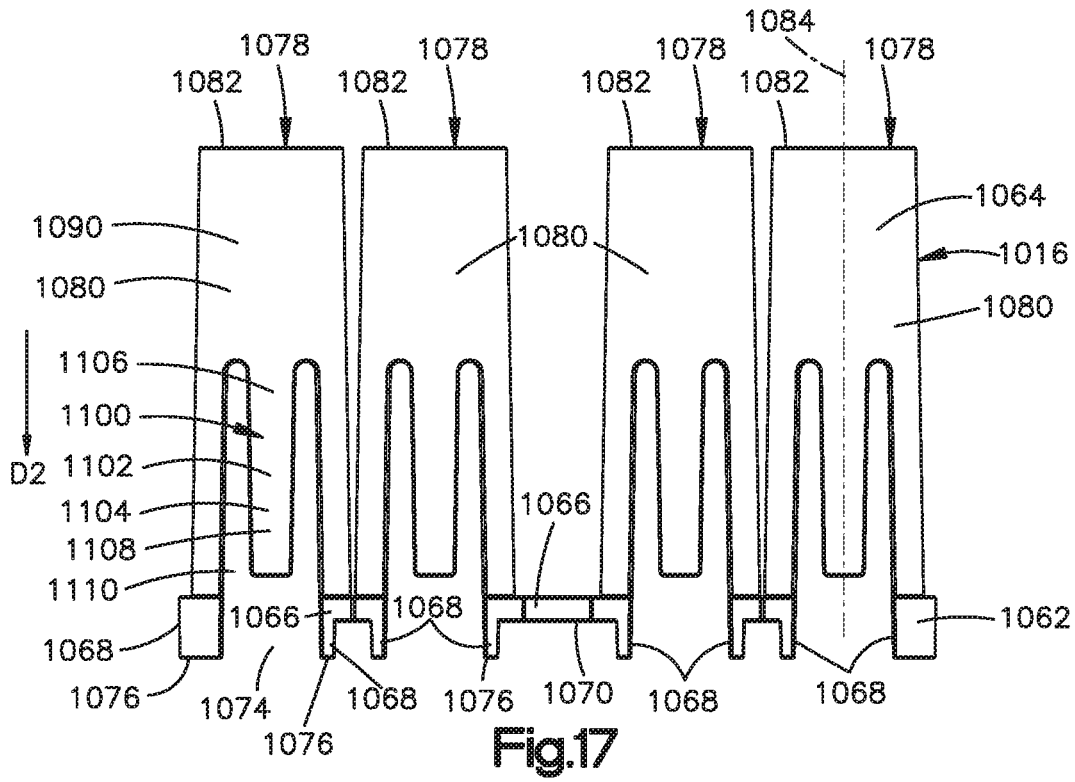
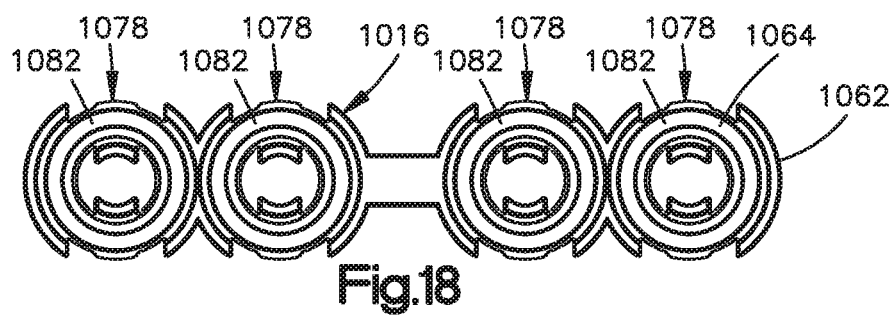
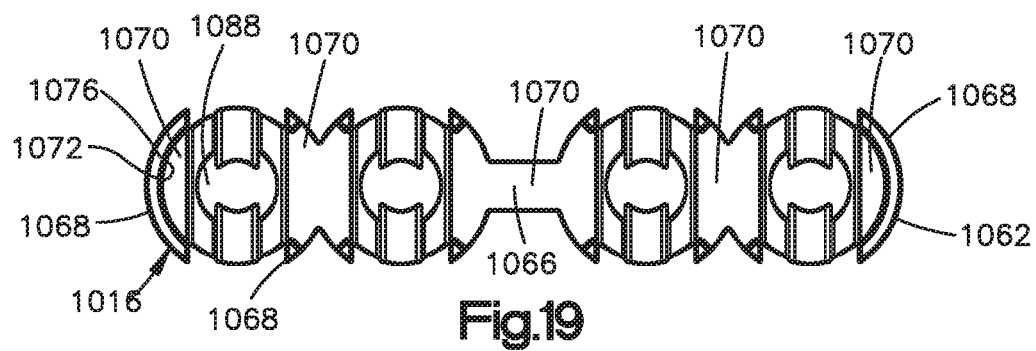

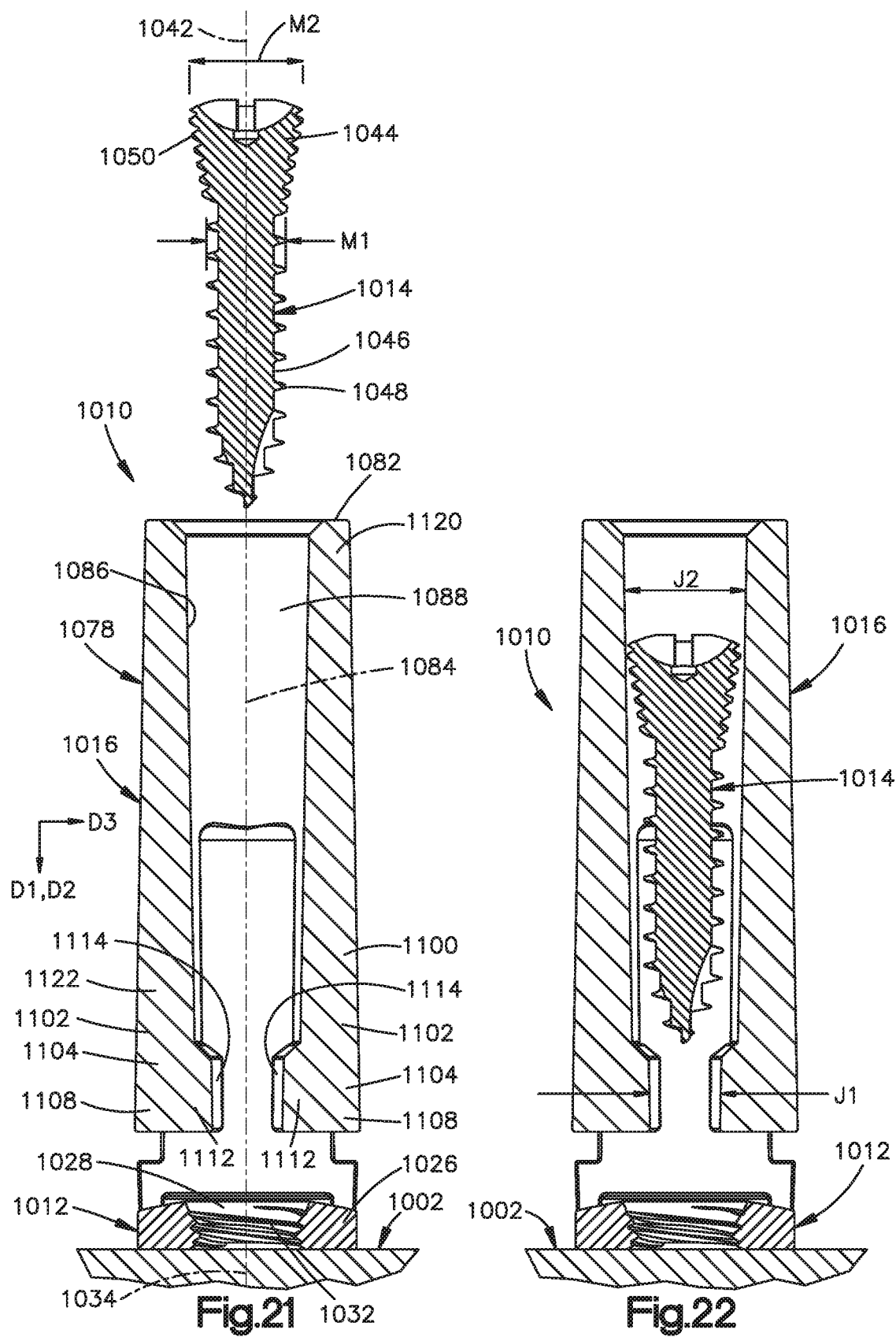

BONE PLATE FASTENING SYSTEM

CROSS REFERENCE TO RELATED APPLICATIONS

This application claims the benefit of U.S. Provisional Application No. 62/439,311 filed Dec. 27, 2016 and U.S. Provisional Application No. 62/516,402 filed Jun. 7, 2017, the disclosures of which are hereby incorporated by reference in their entireties.

TECHNICAL FIELD

The present application relates generally to medical devices. More specifically, the present application is related to devices, systems, kits, and methods for bone fixation.

BACKGROUND

The process of bone fixation using a plate involves a number of steps. The process may include the steps of aligning and engaging a fastener, for example a screw, with the plate. Failure to properly align one of the fasteners with the plate may result in problems, such as generation of a burr. For example, improper alignment of a locking screw may result in generation of a burr as threads on a head of the locking screw head engage with threads of a hole of the plate, or when threads on a shaft of a screw rub against an edge of the hole of the plate.

Another potential consequence of improper alignment of a fastener with the hole of the plate is improper engagement of the head of the fastener, for example the threads on the head of the locking screw, and the hole of the plate, for example the threads within the hole of the plate. Improper engagement of the head of the fastener and the hole of the plate may lead to inadequate securement of the fastener to the plate, stripping of the corresponding threads of at least one of the plate and the screw, or both, any of which may contribute to malunion or non-union of a fractured bone to which the plate is attached.

The difficulty of aligning the fastener with a hole of the bone plate may be increased in certain situations such as when access to the plate is limited, for example during a minimally invasive surgery, or when using a self-drilling screw. A self-drilling screw may be inserted without a pilot hole or guide hole being pre-drilled into the target bone to be fixed. Thus using a self-drilling screw may eliminate some of the steps in a bone fixation process, for example the steps associated with pre-drilling a guide hole. However, at least some of the benefit of using a self-drilling screw may be offset by the increased difficulty from the alignment and the engagement steps of the process.

A device, kit, system, method, or any combination thereof that mitigates the difficulty of aligning and engaging a fastener with a hole of the bone plate may result in an increase in efficiency for bone fixation processes.

SUMMARY

In accordance with an aspect of the disclosure, a screw guide includes a first end, a second end spaced from the first end, a guide body that extends from the first end to the second end, and a guide hole that extends through the guide body. The guide body includes a first guide surface and a second guide surface, the first guide surface defines a first opening of the guide hole. The second surface is spaced from the first surface in a first guide direction, and the second surface defines a second opening of the guide hole. The guide body includes a leg portion that extends from the second guide surface in the first guide direction such that the leg portion is spaced from the second opening in a second guide direction that is perpendicular to the first guide direction. The guide body defines a first guide thickness measured in the first direction from a first point that is both on the first surface, and partially defines the first opening, to a second point that is both on the second surface, and partially defines the second opening. The guide body defines a second guide thickness measured in the first guide direction from a third point that is both on the first guide surface, and aligned with the leg portion with respect to the first guide direction, to a fourth point that is on a surface of the leg portion that is opposite the first guide surface with respect to the first guide direction, and the second guide thickness is greater than the first guide thickness.

In accordance with an aspect of the disclosure, a kit includes a screw guide and a bone plate. The bone plate includes a plate body including a first plate surface and a second plate surface, the second plate surface configured to face a bone. The bone plate includes a plate hole that extends into the first plate surface and through the second plate surface, the first plate surface defines a first opening of the plate hole, and the second plate surface is spaced from the first plate surface. The second plate surface defining a second opening of the plate hole. The kit defines a coupled configuration in which the first opening of the plate hole is aligned with the second opening of the guide hole along the first guide direction and the second guide surface faces the first plate surface.

In accordance with an aspect of the disclosure, a method of securing a fastener to a plate includes the step of coupling a screw guide with the plate such that a guide hole defined by a guide body of the screw guide is aligned with a screw hole defined by a plate body of the plate along a direction. The method further including the steps of inserting the fastener in the direction into the guide hole, during the inserting step, contacting the fastener with the guide body, after the inserting step, contacting the fastener with the plate body, and detaching the screw guide from the plate.

In accordance with an aspect of the disclosure, a method of securing a fastener to a plate includes the step of coupling a screw guide with the plate such that a plate hole is aligned with a screw hole along a direction. The method further includes the steps of inserting the fastener in the direction into the guide hole, during the inserting step, contacting the fastener with the guide body, during the inserting step and after the contacting step, contacting the fastener with the plate body, and detaching the screw guide from the plate.

In accordance with an aspect of the disclosure, a fastener guide configured to align a fastener and a plate is disclosed. The fastener guide includes a plate alignment portion and a fastener alignment portion. The plate alignment portion includes a base and a projection that extends from the base. The fastener alignment portion includes an alignment chamber with a housing and a through hole configured to receive the fastener. The housing extends from the plate alignment portion along a chamber axis in a first direction, and the alignment chamber further includes an alignment mechanism having an abutment surface that faces the chamber axis. The alignment mechanism defines a distance measured from the abutment surface to the chamber axis along a second direction, which is perpendicular to the first direction, and the alignment mechanism is flexible such that the distance is configured to increase as the fastener contacts the abutment surface.

In accordance with an aspect of the disclosure, a kit configured to repair a defect in a surface comprises a plate, a fastener, and a fastener guide. The plate includes a first surface, a second surface opposite the first surface, a side wall that extends between the first surface and the second surface thereby defining an outer perimeter of the plate, a plate hole that extends through both the first surface and the second surface along a hole axis, and an inner surface that extends between the first surface and the second surface and that defines the plate hole. The fastener includes a head and a shaft that extends from the head. The shaft is configured to be inserted through the plate hole and into the surface to secure the plate to the surface.

The fastener guide includes a plate alignment portion and a fastener alignment portion, the plate alignment portion including a base and a projection that extends from the base in a first direction. The base includes a lower surface, and the projection includes an inner surface that is substantially perpendicular to the lower surface. The fastener alignment portion includes an alignment chamber that extends from the plate alignment portion in a second direction, and the alignment chamber includes a housing having an inner surface. The alignment chamber further includes a through hole defined by the inner surface of the housing. The through hole is configured to receive the fastener, and the through hole extends along a chamber axis. The fastener guide is configured to be attached to the plate such that the lower surface of the base faces the first surface of the plate, such that the inner surface of the projection faces the side wall of the plate, and such that the hole axis is collinear with the chamber axis.

In accordance with an aspect of the disclosure, a method of securing a fastener to a plate such that a central axis of the fastener is collinear with a hole axis of the plate is disclosed. The fastener is configured to advance in a first direction to be inserted into a surface, the hole axis extends through a center of a plate hole of the plate, and the plate hole is configured to receive the fastener. The method includes the step of advancing the fastener in the first direction while the fastener is positioned in a through hole of a fastener guide toward the plate hole, the fastener guide being attached to the plate such that movement of the fastener guide relative to the plate in the first direction and in all directions perpendicular to the first direction is blocked by interference of a plate alignment portion of the fastener guide with the plate. The method further includes the step of abutting a shaft of the fastener with an abutment surface of a flexible finger thereby increasing a distance between the abutment surface and the central axis as measured in a direction perpendicular to the first direction, and thereby applying a force to a shaft of the fastener that aligns the central axis with the hole axis such that the central axis and the hole axis are collinear, wherein the flexible finger extends from a housing of the fastener guide, and the housing defines the through hole.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

FIG. 4 is a cross-sectional view of the screw guide and the bone plate illustrated in FIG. 3, along line 4-4 in the unattached configuration;

FIG. 5 is a cross-sectional view of the screw guide and the bone plate illustrated in FIG. 3, along line 4-4 in the attached configuration;

FIG. 6 is an isometric view of the screw guide illustrated in FIG. 1;

FIG. 7 is front elevation view of the screw guide illustrated in FIG. 1

FIG. 8 is a top plan view of the screw guide illustrated in FIG. 1;

FIG. 9 is a side elevation view of the screw guide illustrated in FIG. 1;

FIG. 10 is a bottom plan view of the screw guide illustrated in FIG. 1;

FIG. 11 is a top plan view of a screw guide, according to another aspect of the disclosure;

FIG. 17 is a side elevation view of the fastener guide illustrated in FIG. 12;

FIG. 18 is a top plan view of the fastener guide illustrated in FIG. 12;

FIG. 19 is a bottom plan view of a portion of the fastener guide illustrated in FIG. 12;

FIG. 21 is a cross-sectional view of a portion of the fastener guide, a portion of the bone plate, and the fastener illustrated in FIG. 20, the fastener guide and the bone plate in the attached configuration, and the fastener in a first position;

FIG. 22 is a cross-sectional view of the portion of the fastener guide, the portion of the bone plate, and the fastener illustrated in FIG. 21, the fastener guide and the bone plate in the attached configuration, and the fastener in a second position;

DETAILED DESCRIPTION

Figure 1:
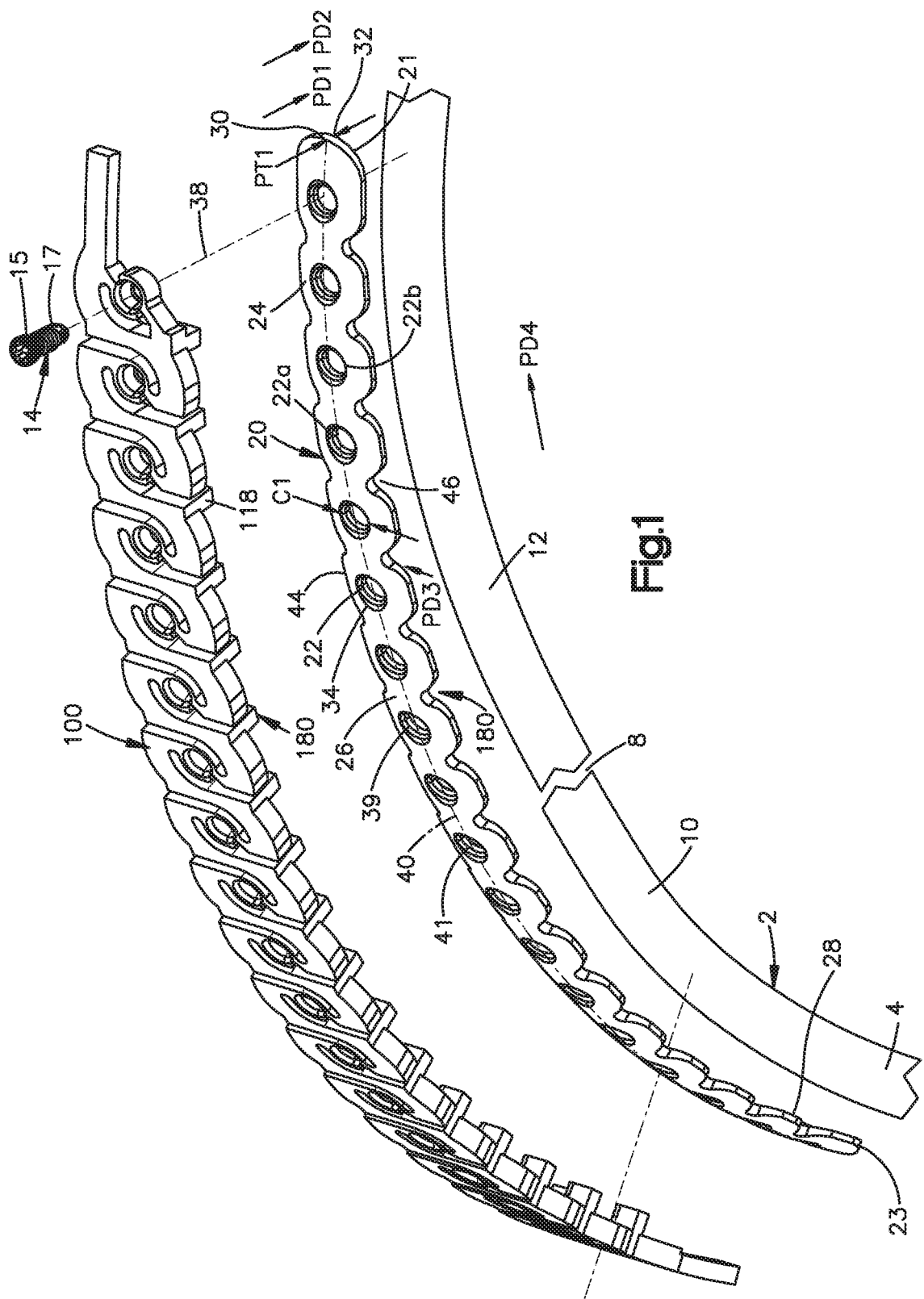
FIG. 1 is an isometric view of a screw guide according to an aspect of the disclosure, and a bone plate, the screw guide and the bone plate in an unattached configuration.

Certain terminology is used in the following description for convenience only and is not limiting. The words "proximal" and "distal" refer to directions toward and away from, respectively, a surgeon using the referenced device. The term "aligned" as used herein in reference to two elements along a direction means a straight line that passes through one of the elements and that is parallel to the direction will also pass through the other of the two elements. The term "between" as used herein in reference to a first element being between a second element and a third element with respect to a direction means that the first element is closer to the second element as measured along the direction than the third element is to the second element as measured along the direction. The term "between" includes, but does not require that the first, second, and third elements be aligned along the direction.

Aspects of the disclosure will now be described in detail with reference to the drawings, wherein like reference numbers refer to like elements throughout, unless specified otherwise. Certain terminology is used in the following description for convenience only and is not limiting. The term "plurality", as used herein, means more than one. The terms "a portion" and "at least a portion" of a structure include the entirety of the structure. Certain features of the disclosure which are described herein in the context of separate embodiments may also be provided in combination in a single embodiment. Conversely, various features of the disclosure that are described in the context of a single embodiment may also be provided separately or in any subcombination.

Referring to FIGS. 1 to 5, a plate 20 is configured to be secured to a structure 2, for example a surface 4 of the structure 2 to stabilize the structure 2. According to one aspect of the disclosure, the structure 2 is a bone 6, and the plate 20 may be configured to be secured to the bone 6, such that the plate 20 is a bone plate. The bone 6 may include a defect 8, such as a fracture, between a first portion 10 of the bone 6 and a second portion 12 of the bone 6. The plate 20 is configured to be secured to both the first portion 10 and the second portion 12 such that the plate 20 bridges the defect 8.

The plate 20 may be configured to be secured to the bone 6 by one or more fasteners 14. The plate 20 and the fastener 14 may define a desired alignment in which the fastener 14 is inserted into a plate hole 22 of the plate 20 such that the plate 20 is secured to the bone 6 optimally. The plate 20 and the fastener 14 may define an undesired alignment in which the fastener 14 is inserted into the plate hole 22 of the plate 20 such that the plate 20 is secured to the bone 6 suboptimally. The plate 20 being optimally secured to the bone 6 by the fastener 14 may include a more secure coupling of the plate 20 to the bone 6 for less chance of back out of the fastener 14 from the plate hole 22, proper engagement of a locking feature of the fastener 14 with a corresponding locking feature of the plate 20, or any combination thereof, among other benefits. The fastener 14 may include self-tapping screws, locking screws, non-locking screws, or any combination thereof.

The plate 20 includes a first end 21, a second end 23, and a plate body 24 that extends between the first end 21 and the second end 23. The plate body 24 includes a first plate surface 26 and a second plate surface 28, the second plate surface 28 opposite the first plate surface 26. The plate 20 is configured to be secured to the bone 6 such that the second plate surface 28 faces, for example contacts, the bone 6. The plate 20 defines a plate thickness PT1 measured from the first plate surface 26 to the second plate surface 28. As shown the plate thickness PT1 may be measured from a first point 30 on the first plate surface 26 to a second point 32 on the second plate surface 28 along a first plate direction PD1 that is normal to the first plate surface 26 at the first point 30 and normal to the second plate surface 28 at the second point 32.

The plate hole 22 extends into the first plate surface 26 and through the second plate surface 28, such that the plate hole extends through an entirety of the plate thickness PT1 along a second plate direction PD2. As shown in the illustrated embodiment, the first plate direction PD1 may be parallel to the second plate direction PD2. Alternatively, the first plate direction PD1 may be non-parallel with the second plate direction PD2. As shown in the illustrated embodiment, the plate hole 22 may extend along a plate hole axis 38. The plate hole axis 38 may be a central axis according to one embodiment. The plate hole axis 38 may be an off-center axis according to another embodiment.

The plate body 24 may include a plate inner surface 39 that extends between the first plate surface 26 and the second plate surface 28, and that defines the plate hole 22. The plate inner surface 39 may include a locking feature 41, for example threads, configured to engage with the fastener 14, for example a head 15 of the fastener 14 that may include corresponding threads.

The first plate surface 26 defines a first opening 34 of the plate hole 22, and the second plate surface 28 defines a second opening 36 of the plate hole 22. The plate hole 22 defines a first cross-sectional dimension C1 measured in a third plate direction PD3 that is entirely within a plane that the second plate direction PD2 is normal to. The first cross-sectional dimension C1 may be a maximum cross-sectional dimension. The first cross-sectional dimension C1 may be measured at the first opening 34, at the second opening 36 or at a location between the first opening 34 and the second opening 36.

The plate 20 may include a plurality of plate holes and the plate hole 22 may be one of the plurality of plate holes. Each of the plurality of plate holes may be spaced from adjacent ones of the plurality of plate holes along a longitudinal axis 40 of the plate 20. The longitudinal axis 40 may be straight, curved, or partially straight and partially curved. A first plate hole 22a may be spaced from a second plate hole 22b along a fourth plate direction PD4. The fourth plate direction PD4 may be substantially perpendicular to the first plate direction PD1, the second plate direction PD2, the third plate direction PD3, or any combination thereof.

The plate body 24 includes a first plate side surface 42 and a second plate side surface 44 spaced from the first plate side surface 42 in a fifth plate direction PD5. The plate defines a plate width PW1 measured from the first plate side surface 42 to the second plate side surface 44 along the fifth plate direction PD5. The plate 20 may include one or more notches 46 defined by the first plate side surface 42, the second plate side surface 44, or both such that the plate width PW1 measured at a location aligned with one of the notches 46 in the fifth plate direction PD5 is less than the plate width PW1 measured at a location not aligned with one of the notches 46 in the fifth plate direction PD5.

The plate body 24 may be configured to be flexible such that the first end 21 is movable with respect to the second end 23. According to one embodiment, the plate 20 is configured such that the first end 21 is translatable relative to the second end 23, is rotatable relative to the second end 23, or both.

Referring to FIGS. 4 to 10, a screw guide 100 is configured to be secured to a plate, for example the plate 20, to assist in achieving the desired alignment of the fastener 14 and the plate 20. The screw guide 100 includes a first end 102, a second end 104 spaced from the first end 102, a guide body 106 that extends from the first end 102 to the second end 104, and a guide hole 108 that extends through the guide body 106. The guide body 106 includes a first guide surface 110 and a second guide surface 112. The first guide surface 110 defines a first opening 114 of the guide hole 108, and the second guide surface 112, which is spaced from the first guide surface 110 in a first guide direction GD1, defines a second opening 116 of the guide hole 108.

The guide body 106 includes an attachment structure configured to releasably couple the screw guide 100 to the plate 20. As shown in the illustrated embodiment, the attachment structure may include a leg portion 118 that extends from the second guide surface 112 in the first guide direction GD1. The guide body 106 may be configured such that the leg portion 118 is offset from the second opening 116 in a second guide direction GD2 that is perpendicular to the first guide direction GD1.

The guide body 106 defines a first guide thickness GT1 measured in the first guide direction GD1 from a first point 120 that is on the first guide surface 110 to a second point 122 that is on the second guide surface 112 in the first guide direction GD1. The first point 120 may be coplanar with a plane that entirely defines the first opening 114, the first point 120 may partially define the first opening 114, or both. The second point 122 may be coplanar with a plane that entirely defines the second opening 116, the second point 122 may partially define the second opening 116, or both. The guide body 106 defines a second guide thickness GT2 measured in the first guide direction GD1 from a third point 124 to a fourth point 126. The third point 124 is on the first guide surface 110 and the third point 124 is aligned with the leg portion 118 with respect to the first guide direction GD1. The second guide thickness GT2 is greater than the first guide thickness GT1.

As shown in the illustrated embodiment, the guide body 106 may include a plurality of attachment portions, for example a plurality of leg portions 118, such that the leg portion 118 is a first of the plurality of leg portions 118. The plurality of leg portions 118 may include a pair of leg portions 118 offset from one another in the second guide direction GD2. The pair of leg portions 118 may include a first leg portion 118a and a second leg portion 118b. As shown in the illustrated embodiment, the first leg portion 118a and the second leg portion 118b may be aligned with respect to the second guide direction GD2.

The leg portion 118 may include an inner surface 128 and an outer surface 130 that is offset from the inner surface 128 with respect to the second guide direction GD2. The guide body 106 may be configured such that the inner surface 128 of the first leg portion 118a faces and is aligned with the inner surface 128 of the second leg portion 118b. The inner surface 128 of the first leg portion 118a may be spaced from the inner surface 128 of the second leg portion 118b in the second guide direction GD2 so as to define a gap 132 that defines a gap width GW1 measured in the second guide direction GD2.

The leg portion 118 includes a proximal portion 134 coupled to the second guide surface 112, and the leg portion 118 includes a distal portion 136 spaced from the proximal portion 134 in the first guide direction GD1. The leg portion 118 may include an end surface 138 at which the leg portion 118 terminates in the first guide direction GD1. The fourth point 126 may be positioned on the end surface 138.

According to one aspect of the leg portion 118 includes a lateral extension 140 that extends from the inner surface 128 either in the second guide direction GD2 or a direction opposite the second guide direction GD2. The lateral extension 140 may include an upper surface 142 that faces the second guide surface 112, and that is offset from the second guide surface 112 in the first guide direction GD1 such that a gap height GH1 is defined. The gap height GH1 is measured from the second guide surface 112 to the upper surface 142 in the first guide direction GD1.

The lateral extension 140 may be defined by the distal portion 136. As shown in the illustrated embodiment, the first leg portion 118a and the second leg portion 118b may each include respective lateral extensions 140 that extend toward each other such that the gap width GW1 measured between the respective lateral extensions 140 is less than the gap width GW1 measured between the respective inner surfaces 128 at a location offset from the lateral extensions 140 with respect to the first guide direction GD1.

According to another aspect of the disclosure, the leg portion 118 may be devoid of the lateral extension 140. The inner surfaces 128 of the first leg portion 118a and the second leg portion 118b may be parallel such that the gap width GW1 is constant along the first guide direction GD1. The inner surfaces 128 of the first leg portion 118a and the second leg portion 118b may be nonparallel such that the gap width GW1 tapers along the first guide direction GD1, for example is smaller at either of the distal portion 136 or the proximal portion 134 compared to at the other of the distal portion 136 and the proximal portion 134.

The screw guide 100 may include a plurality of guide holes 108 such that the guide hole 108 is a one of the plurality of guide holes 108. The plurality of guide holes 108 may include a first guide hole 108a and a second guide hole 108b, the second guide hole 108b spaced from the first guide hole 108a in a third guide direction GD3 that is substantially perpendicular to both the first guide direction GD1 and the second guide direction GD2.

According to one aspect of the disclosure, one or more of the leg portions 118, for example the pair of leg portions 118 including the first leg portion 118a and the second leg portion 118b may extend from the second guide surface 112 at a location that is between adjacent ones of the plurality of guide holes 108, for example the first guide hole 108a and the second guide hole 108b with respect to the third guide direction GD3. According to another aspect of the disclosure, one or more of the leg portions 118 may be aligned with one of the guide holes 108 with respect to the second guide direction GD2.

The guide body 106 includes a first side surface 144 and a second side surface 146, that each extend between the first guide surface 110 and the second guide surface 112. The first side surface 144 is opposite the second side surface 146 with respect to the second guide direction GD2. As shown in the illustrated embodiment, the screw guide 100 may include a first recess 148. The first recess 148 may include a first recess opening 150 defined by the first guide surface 110, a second recess opening 152 defined by the second guide surface 112, a third recess opening 154 defined by one of the first side surface 144 and the second side surface 146, or any combination of the first recess opening 150, the second recess opening 152, and the third recess opening 154.

According to one aspect of the disclosure, at least a portion of the first recess 148 may be between adjacent ones of the plurality of guide holes 108 with respect to the third guide direction GD3, may be aligned with adjacent ones of the plurality of guide holes 108 with respect to the third guide direction GD3, or both. The screw guide 100 may include a second recess 156. The second recess 156 may include a first recess opening defined by the first guide surface 110, a second recess opening defined by the second guide surface 112, a third recess opening defined by one of the first side surface 144 and the second side surface 146, or any combination thereof.

According to one embodiment, the third recess opening 154 of the first recess 148 may be defined by the first side surface 144, and the third recess opening of the second recess 156 may be defined by the second side surface 146. According to another embodiment, the third recess opening 154 of the first recess 148 and the third recess opening of the second recess 156 may both be defined by the same surface, for example the first side surface 144. At least a portion of the second recess 156 may be between adjacent ones of the plurality of guide holes 108 with respect to the third guide direction GD3, may be aligned with adjacent ones of the plurality of guide holes 108 with respect to the third guide direction GD3, or both.

The screw guide 100 may include a plurality of the first recesses 148, a plurality of the second recesses 156, or a plurality of both. The screw guide 100 may include the plurality of first recesses 148 arranged alternatingly with the plurality of second recesses 156 along the third guide direction GD3. The screw guide may include both a first recess 148 and a second recess 156 between adjacent ones of the plurality of guide holes 108 with respect to the third guide direction GD3, aligned with adjacent ones of the plurality of guide holes 108 with respect to the third guide direction GD3, or both.

The guide hole 108 extends along a guide hole axis 158 from the first opening 114 to the second opening 116. The guide hole axis 158 may be a central axis according to one embodiment. The guide hole axis 158 may be an off-center axis according to another embodiment. The guide hole axis 158 may be parallel to the first guide direction GD1 in one embodiment, or non-parallel to the first guide direction GD1 in another embodiment.

According to one aspect of the disclosure, the guide body 106 may be configured to be flexible such that the first end 102 is movable with respect to the second end 104. According to one embodiment, the screw guide 100 is configured such that the first end 102 is translatable relative to the second end 104, is rotatable relative to the second end 104, or both. The guide body 106 may be flexible such that the first end 102 is movable relative to the second end 104 in the first guide direction GD1, the second guide direction GD2, the third guide direction GD3, or any combination thereof. The guide body 106 may be flexible such that the first end 102 is rotatable relative to the second end 104 about at least one of a first axis that is parallel to the first guide direction GD1, a second axis that is parallel to the second guide direction GD2, and a third axis that is parallel to the third guide direction GD3. One or more of the first axis, the second axis, and the third axis may intersect the guide hole 108.

The guide body 106 may be flexible such that in a first configuration the respective guide hole axes 158 of adjacent ones of the plurality of guide holes 108 are parallel, and in a second configuration the respective guide hole axes 158 of adjacent ones of the plurality of guide holes 108 are non-parallel. According to one embodiment, the guide body 106 is configured such that screw guide 100 is capable of transition between the first configuration and the second configuration without plastic deformation of the screw guide 100. According to another embodiment, the guide body 106 is capable such that the screw guide 100 is capable of transition between the first configuration and the second configuration by plastic deformation of the screw guide 100. The guide body 106 being flexible as described above may allow the guide body 106 to be used with a plurality of different plates, including plates configured to be contoured to match surfaces, such as bones, with a high degree of curvature or with complex geometries.

According to one embodiment, the first guide surface 110 may define an enclosed perimeter of the first opening 114, the second guide surface 112 may define an enclosed perimeter of the second opening 116, or both. According to one embodiment, the enclosed perimeter of the first opening 114, the second opening 116, or both includes a frangible portion 164 configured such that during movement of the fastener 14 through the guide hole 108 the frangible portion 164 plastically deforms. The frangible portion 164 may be configured such that movement of the fastener 14 through the guide hole 108 ruptures the frangible portion 164 such that the first guide surface 110 no longer defines an enclosed perimeter of the first opening 114, such that the second guide surface 112 no longer defines an enclosed perimeter of the second opening 116, or both.

The guide body 106 may include a grip member 166 configured to be grabbed and have a force applied to the grip member 166 to decouple the screw guide 100 from the plate 20. The grip member 166 may include a first tab 168 positioned closer to the first end 102 than the guide hole 108 is positioned to the first end 102, a second tab 170 positioned closer to the second end 104 than the guide hole 108 is positioned to the second end 104, or both. The first tab 168 and the second tab 170 may be positioned on the guide body 106 such that all of the plurality of guide holes 108 are between the first tab 168 and the second tab 170 with respect to the third guide direction GD3.

The first tab 168 includes a first tab surface 172 and a second tab surface 174 spaced from the first tab surface 172 in the first guide direction GD1, the guide body 106 defines a third guide thickness GT3 measured in the first guide direction GD1 from the first tab surface 172 to the second tab surface 174, such that the first guide thickness GT1 is greater than the third guide thickness GT3. The first tab surface 172 may be monolithic with the first guide surface 110, planar with the first guide surface 110, or both.

The guide hole 108 defines a second cross-sectional dimension C2 measured in a direction that is entirely within a plane that the first guide direction GD1 is normal to. For example, the second cross-sectional dimension C2 may be measured in the second guide direction GD2, the third guide direction GD3, or another direction that includes components of both the second guide direction GD2 and the third guide direction GD3. The second cross-sectional dimension C2 may be a maximum cross-sectional dimension of the guide hole 108. The second cross-sectional dimension C2 may be measured at the first opening 114, at the second opening 116, or at a location between the first opening 114 and the second opening 116.

Referring to FIG. 11, according to another embodiment the guide body 106 may be configured such that the first guide surface 110 is devoid of any recesses that are aligned with the guide hole axes 158 of adjacent ones of the plurality of guide holes 108. As shown in the illustrated embodiment, a line 176 that extends through both guide hole axes 158 of adjacent ones of the plurality of guide holes 108 does not intersect a recess, for example the recess 148 and the second recess 156 (shown in FIGS. 6 to 10).

Referring to FIGS. 4 and 5, a bone fixation system includes a kit 200, and the kit 200 may include the screw guide 100 and a plate, for example the plate 20. The kit 200 may further include one or more of the fasteners 14. According to one embodiment, the kit 200 may include a plurality of the screw guide 100, a plurality of the plate 20, a plurality of the fasteners 14, or any combination thereof. The screw guide 100 and the plate 20 may define an attached configuration wherein the second guide surface 112 faces the first plate surface 26, and the plate hole 22 is aligned with the guide hole 108. The plate thickness PT1 may be substantially equal to the gap height GH1 such that in the attached configuration the plate 20 is positioned in the gap 132 such that the second guide surface 112 faces the first plate surface 26 and the upper surface 142 faces the second plate surface 28.

The first cross-sectional dimension C1 may be greater than the second cross-sectional dimension C2, as shown in the illustrated embodiment. According to another embodiment, the first cross-sectional dimension C1 may be equal to the second cross-sectional dimension C2.

Figure 2:
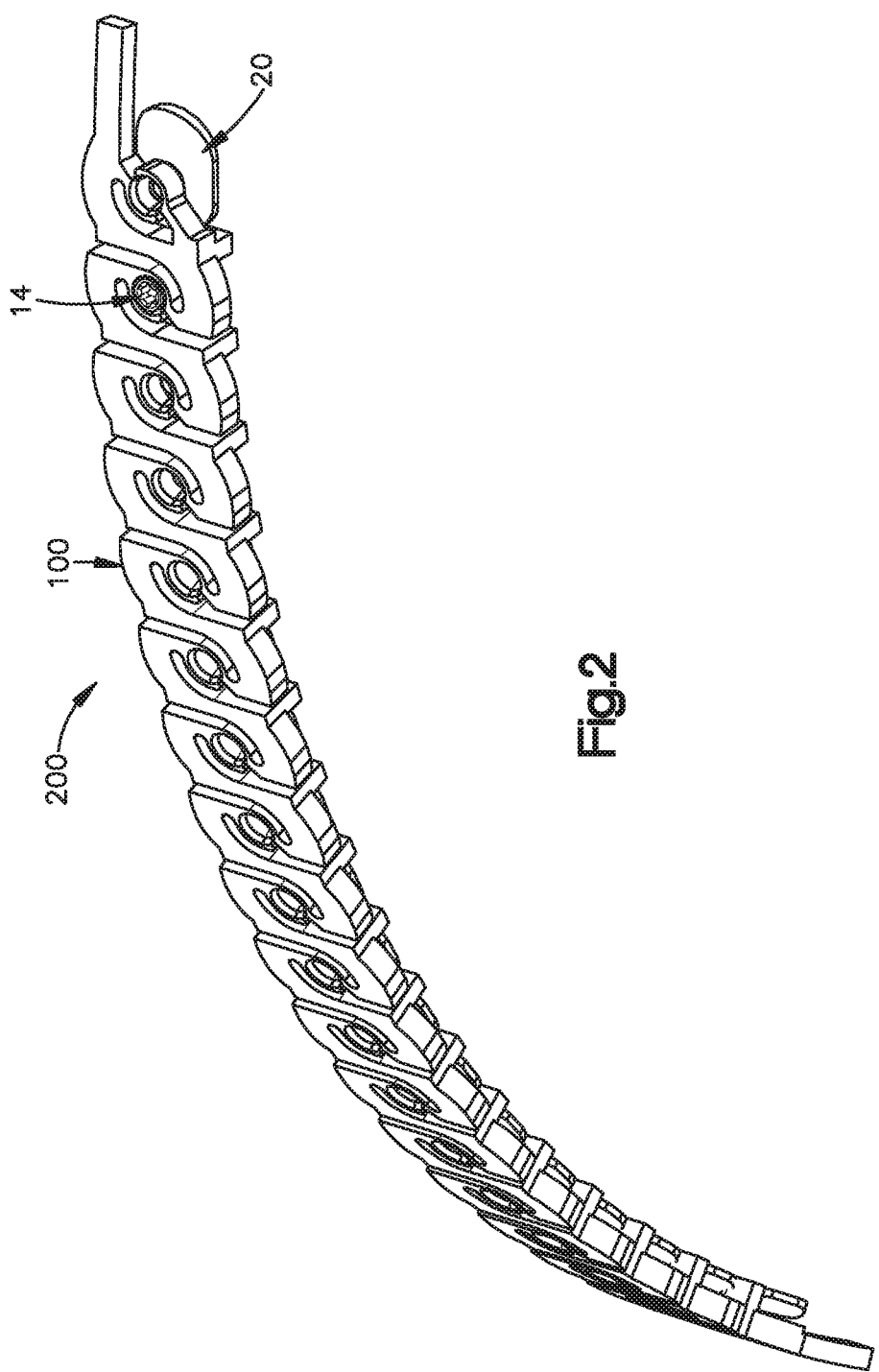
FIG. 2 is an isometric view of the screw guide and the bone plate illustrated in FIG. 1, in an attached configuration.
Figure 3:
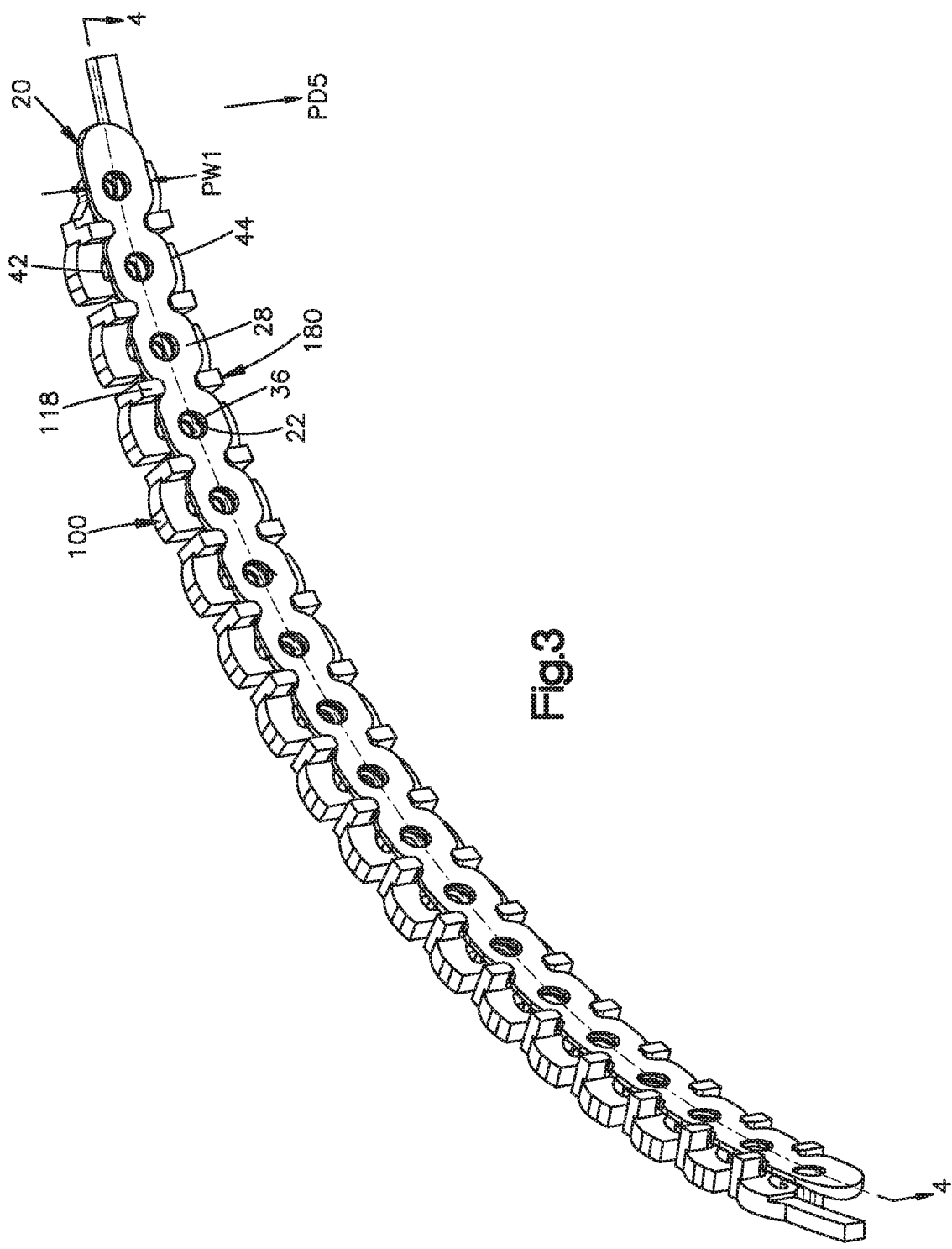
FIG. 3 is another isometric view of the screw guide and the bone plate illustrated in FIG. 1, in an attached configuration.

Referring to FIGS. 1 to 3, the kit 200 may include an alignment mechanism 180 configured to assist in aligning the plate hole 22 and the guide hole 108. As shown in the illustrated embodiment, the alignment mechanism 180 may include the notch 46 and the leg portion 118. The plate 20 and the screw guide 100 are configured such that when the leg portion 118 is positioned within the notch 46, or a plurality of the leg portions 118 are positioned within a plurality of the notches 46, the plate hole 22 is aligned with the guide hole 108.

Referring to FIGS. 1 to 11, a method of securing the fastener 14 to the plate 20 includes the step of attaching the screw guide 100 to the plate 20 such that the guide hole 108 is aligned with the plate hole 22 along an insertion direction, the insertion direction may be parallel to the first plate direction PD1, parallel to the first guide direction GD1, or parallel to both the first plate direction PD1 and the first guide direction GD1. The method may further include the step of inserting the fastener 14 in the insertion direction into the guide hole 108.

According to one embodiment, the method may include the step of contacting the fastener 14 with the guide body 106 during the inserting step. The step of contacting the fastener 14 with the guide body 106 may include the step of contacting a shaft 17 of the fastener 14 with an inner surface 115 of the guide body 106 that defines the guide hole 108.

The shaft 17 may define a third cross-sectional dimension C3 that is substantially equal to the second cross-sectional dimension C2. The method may further include the step of contacting the fastener 14 with the plate 20. The head 15 of the fastener 14 may define a fourth cross-sectional dimension C4 that is substantially equal to the first cross-sectional dimension C1. The kit 200 may include a plurality of the fasteners 14 in addition to one or more of the plate 20 and one or more of the screw guide 100.

The method may further include the step of contacting the fastener 14 with the plate body 24 after the inserting step. The method may further include the step of detaching the screw guide 100 from the plate 20. According to one embodiment, the coupling step may include the step of aligning a plurality of the guide holes 108 with a plurality of the screw holes 22. According to one embodiment, the coupling step includes the step of facing the second guide surface 112 with the first plate surface 26. The coupling step may further include the step of inserting the plate body 24 into the gap 132.

According to one embodiment, the step of contacting the fastener 14 may include the step of plastically deforming the guide body 106. According to one embodiment, the step of contacting the fastener 14 with the guide body 106 includes the step of elastically deforming the guide body 106. The method may further include the step of flexing the guide body 106 such that the first end 102 moves relative to the second end 104 in the first guide direction GD1, the second guide direction GD2, the third guide direction GD3, or any combination thereof. The flexing step may include the step of rotating the first end 102 relative to the second end 104 about at least one of a first axis parallel to the first guide direction GD1, a second axis parallel to the second guide direction GD2, and a third axis parallel to the third guide direction GD3.

According to one embodiment, a method of securing the fastener 14 to the plate 20 includes the step of attaching the screw guide 100 to the plate 20 such that the guide hole 108 is aligned with the plate hole 22 along an insertion direction. The method may further include the step of inserting the fastener 14 in the insertion direction into the guide hole 108, during the inserting step, contacting the fastener 14 with the guide body 106. The method may further include, during the inserting step and after the contacting step, the step of contacting the fastener 14 with the plate body 24, and then decoupling the screw guide from the plate 20.

The coupling step may include the step of inserting the plate body 24 into the gap 132. The step of contacting the fastener 14 with the guide body 106 may include the step of plastically deforming the guide body 106, elastically deforming the guide body 106, or both.

Figure 12:
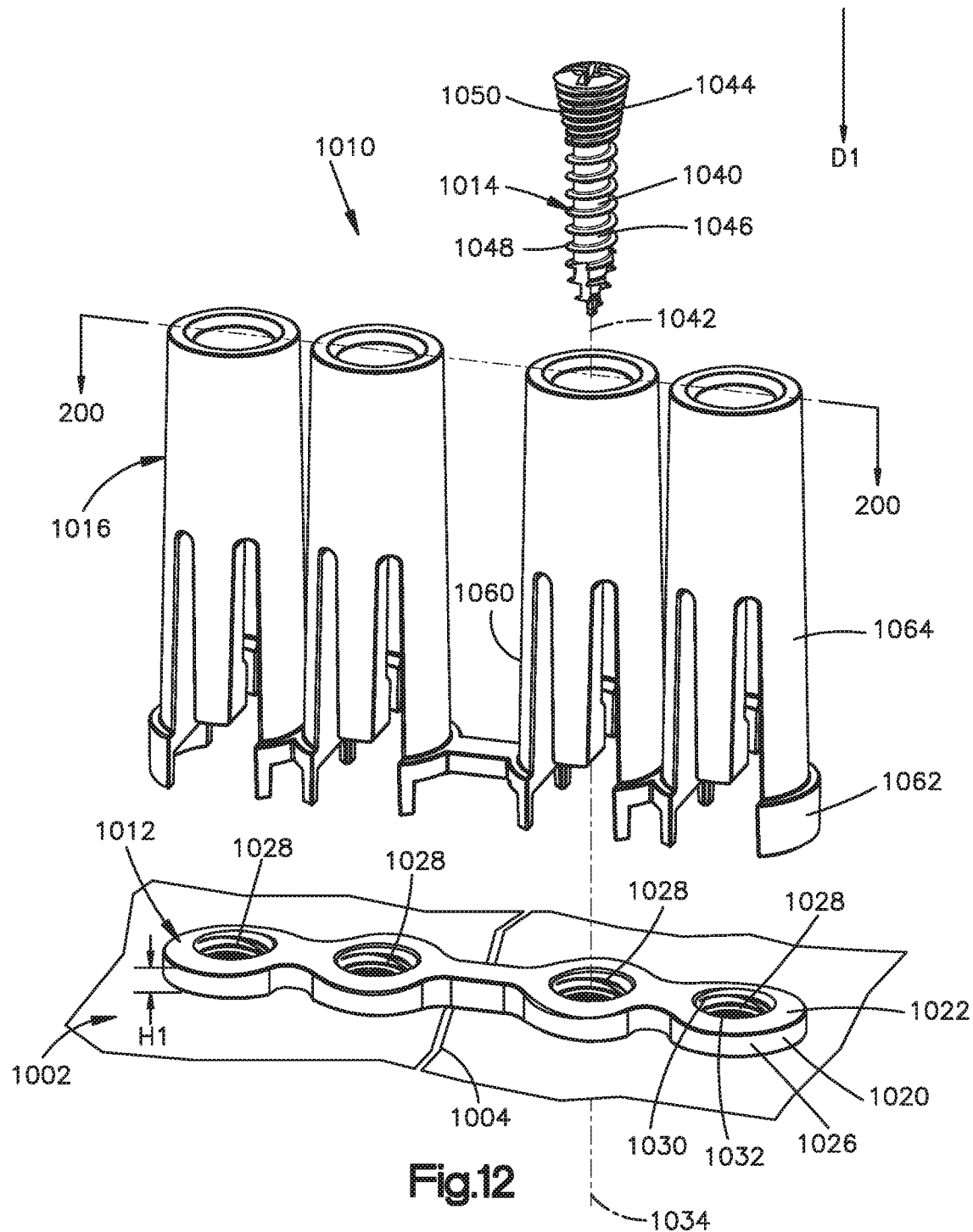
FIG. 12 is an isometric view of a fastener guide according to an aspect of the disclosure, a bone plate, and a fastener, the fastener guide and the bone plate in an unattached configuration.
Figure 13:
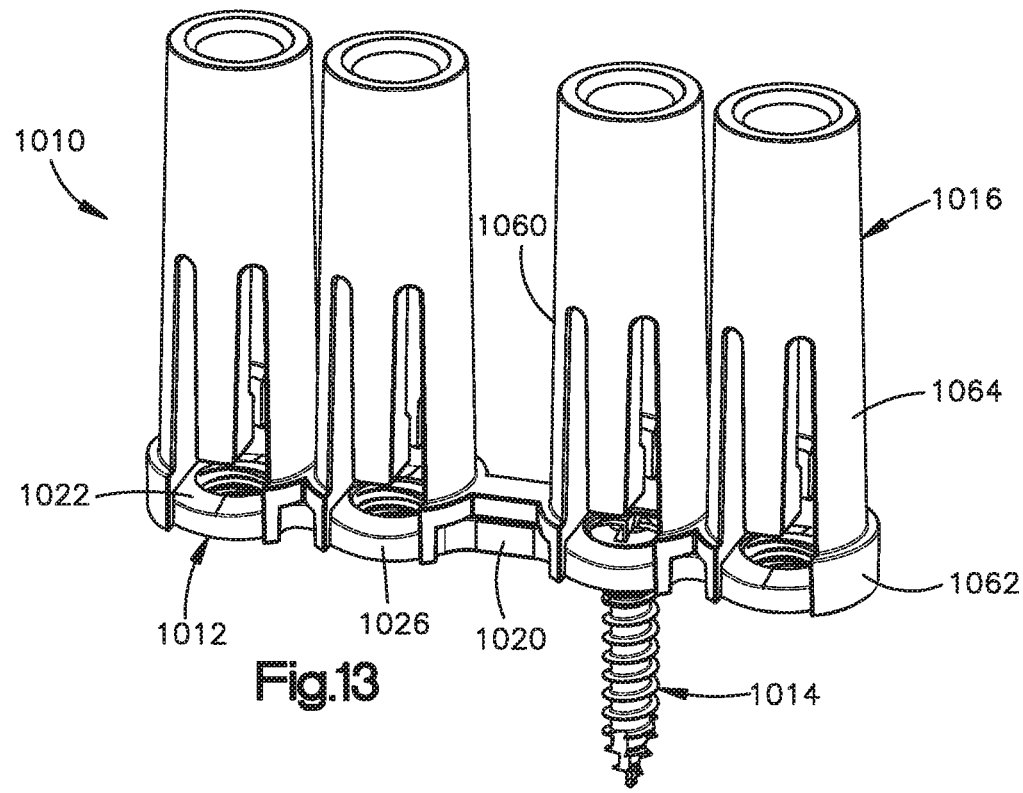
FIG. 13 is an isometric view of the fastener guide, the bone plate, and the fastener illustrated in FIG. 12, the fastener guide and the bone plate in an attached configuration.
Figure 14:
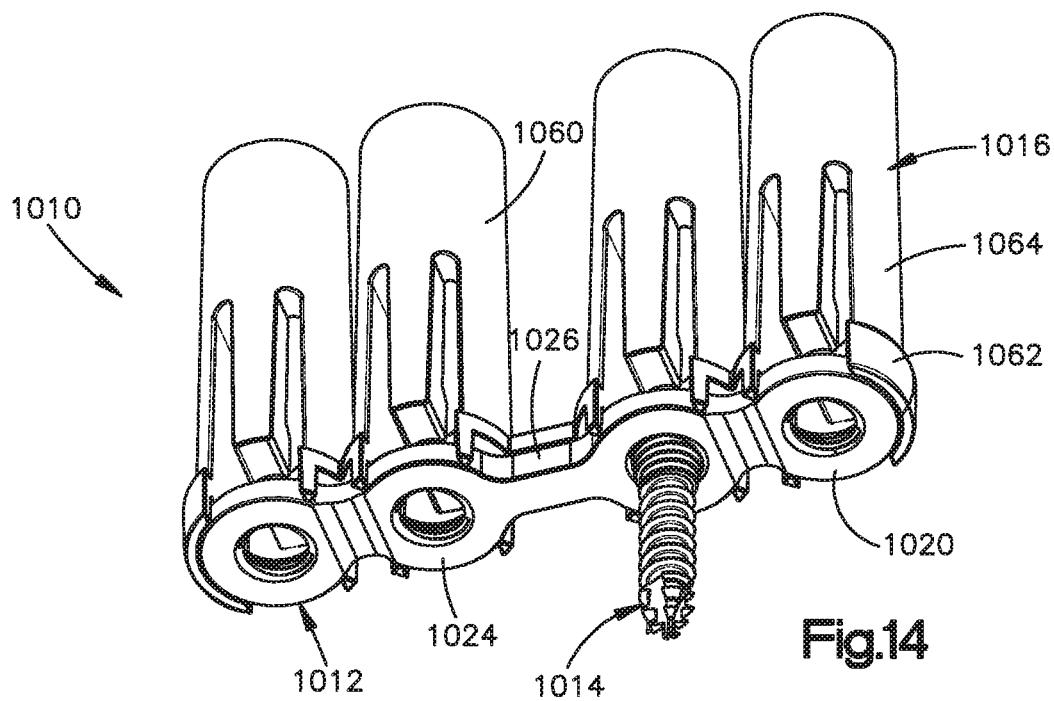
FIG. 14 is another isometric view of the fastener guide, the bone plate, and the fastener illustrated in FIG. 12, in the attached configuration.
Figure 15:
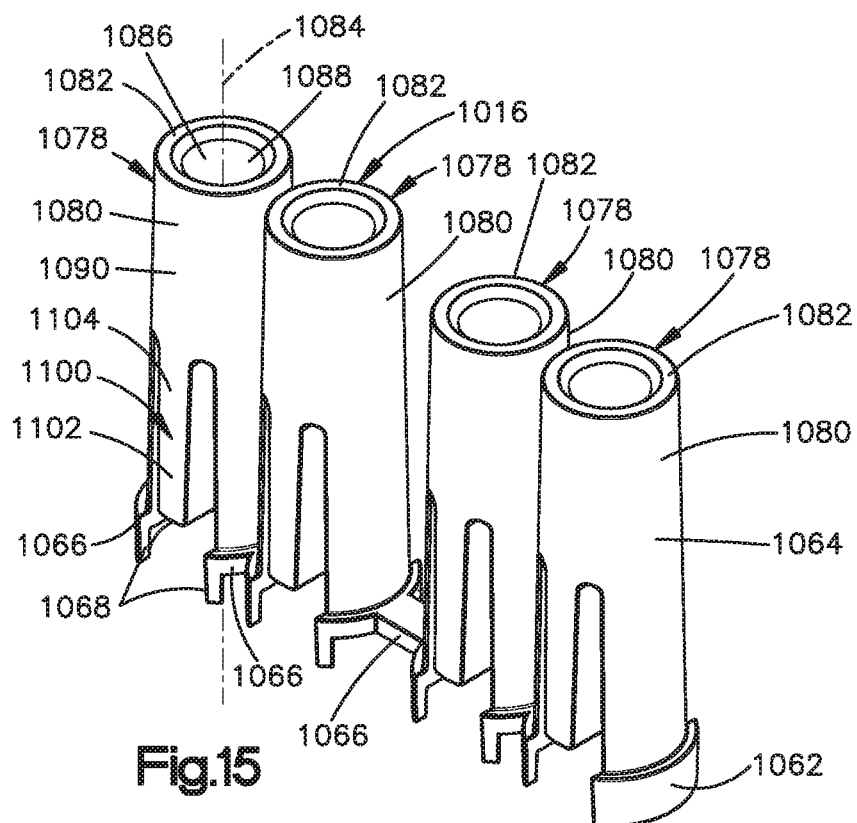
FIG. 15 is an isometric view of the fastener guide illustrated in FIG. 12.
Figure 16:
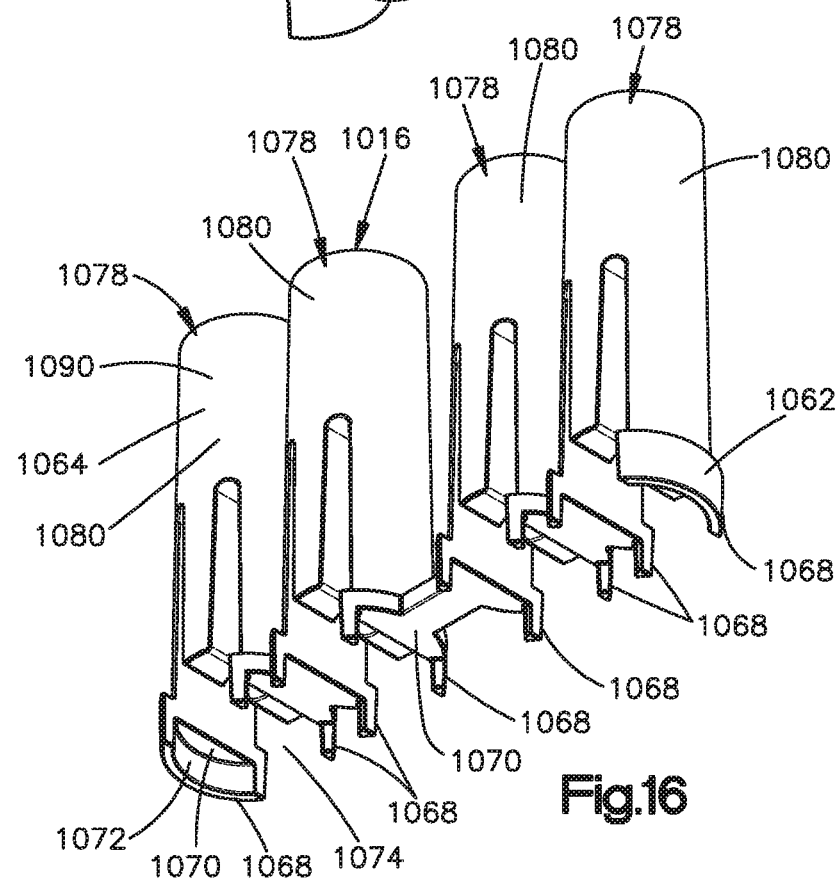
FIG. 16 is another isometric view of the fastener guide illustrated in FIG. 12.
Figure 20:
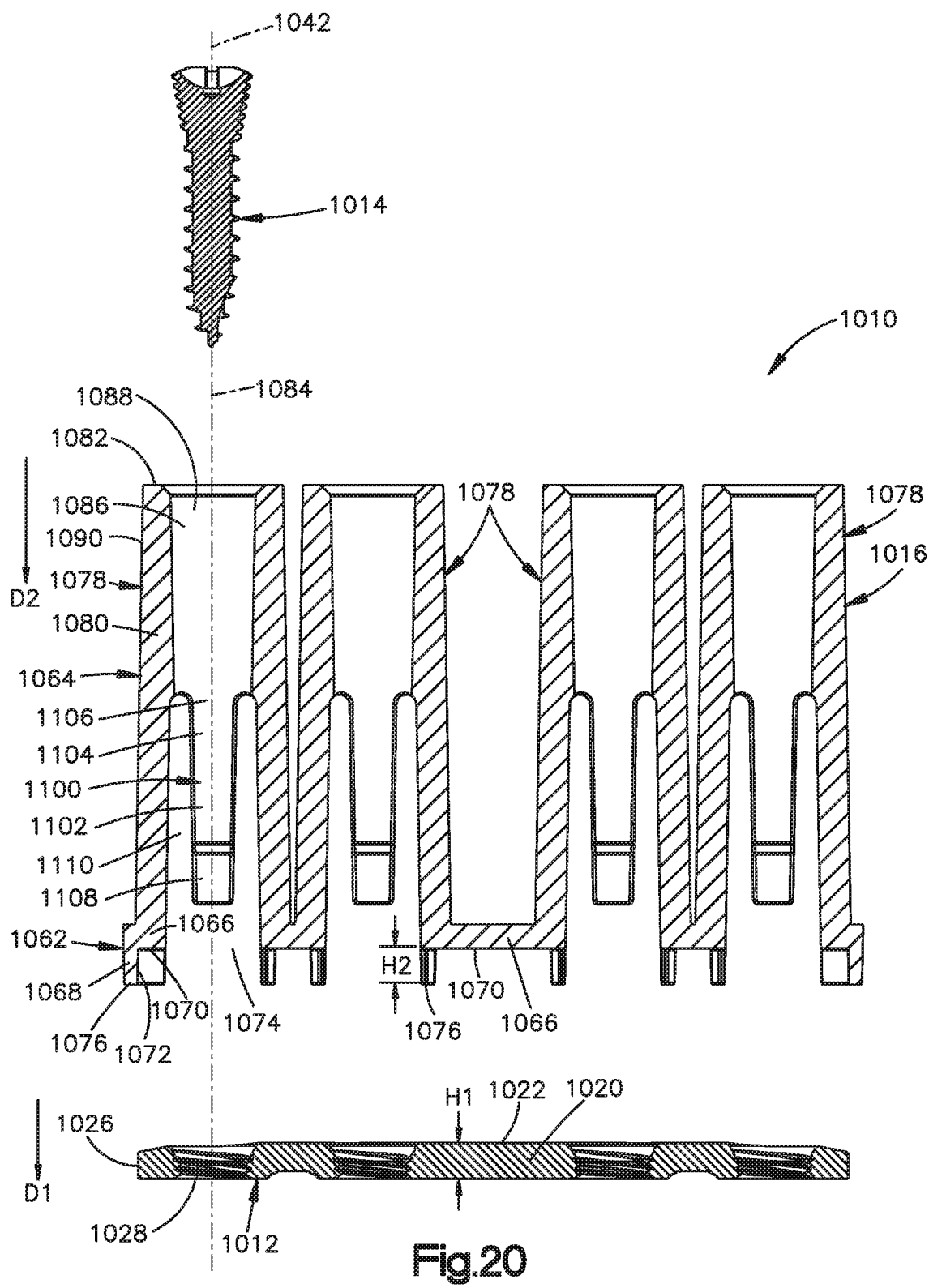
FIG. 20 is a cross-sectional view of the fastener guide, the bone plate, and the fastener illustrated in FIG. 12, along line 200-200, in the unattached configuration.

Referring to FIGS. 12 to 14, a kit 1010 is configured to repair a defect 1004, for example a fracture, in a surface 1002, the kit 1010 includes a plate 1012, a fastener 1014, a fastener guide 1016, or any combination thereof. According to one embodiment of the disclosure, the kit 1010 includes one or more of the plate 1012, one or more of the fastener 1014, one or more of the fastener guide 1016, or any combination thereof. The plate 1012 is configured to be attached to the surface 1002, for example bone, such that relative movement of the plate 1012 and the surface 1002 is prevented. The fastener 1014 is configured to be inserted through the plate 1012 and into the surface 1002, thereby attaching the plate 1012 to the surface 1002 and preventing relative movement of the plate 1012 and the surface 1002. According to one embodiment, a plurality of the fasteners 1014 may be inserted through the plate 1012 and into the surface 1002, thereby attaching the plate 1012 to the surface 1002 and preventing relative movement of the plate 1012 and the surface 1002.

According to one embodiment, the plate 1012 is attached to the surface 1002, such that the plate 1012 straddles the defect 1004 in the surface 1002. The plate 1012 may be secured to the surface 1002 by one of the fasteners 1014 being inserted through the plate 1012 and into the surface 1002 on one side of the defect 1004, and another of the fasteners 1014 being inserted through the plate 1012 and into the surface 1002 on the other side of the defect 1004.

As shown in the illustrated embodiment, the plate 1012 includes a plate body 1020, the plate body 1020 having a first surface 1022 and a second surface 1024, the second surface 1024 being spaced from and opposite the first surface 1022 with respect to a first direction D1. The plate body 1020 further includes a side wall 1026 that extends between the first surface 1022 and the second surface 1024. As shown in the illustrated embodiment, the side wall 1026 may define an outer perimeter of the plate 1012. The plate 1012 defines a plate height H1 measured from the first surface 1022 to the second surface 1024 along the first direction D1. According to one embodiment, the plate height H1 is constant within the perimeter of the plate 1012. According to another embodiment, the plate height H1 varies within the perimeter of the plate 1012 such that the plate 1012 defines a maximum plate height H1 and a minimum plate height H1, which are the largest and smallest values for the plate height H1, respectively.

The plate 1012 further includes a plate hole 1028 that is defined by the plate body 1020, such that the plate hole 1028 extends along a hole axis 1034 through both the first surface 1022 and the second surface 1024. The hole axis 1034 may be parallel to the first direction D1, or non-parallel to the first direction D1. As shown in the illustrated embodiment, the plate 1012 may include a plurality of plate holes 1028. Each of the plurality of plate holes 1028 extends along the respective hole axis 1034, which may be parallel to the first direction D1, or non-parallel to the first direction D1.

The plate hole 1028 is configured to receive a fastener, such as the fastener 1014, to attach the plate 1012 to the surface 1002. An inner surface 1030 of the plate body 1020 may define at least a portion of the plate hole 1028. The inner surface 1030 may be unthreaded, partially threaded, or fully threaded, such that the plate hole 1028 is configured to receive a nail, a non-locking screw, such as a compression screw, a locking screw, or any combination thereof. According to an embodiment of the disclosure, the inner surface 1030 may include threads 1032 configured to engage with corresponding threads on a locking screw.

The fastener 1014 includes a fastener body 1040 that extends along a fastener axis 1042. The fastener axis 1042 may be a central axis, such that the fastener axis 1042 intersects a center of the fastener body 1040. The fastener body 1040 includes a head 1044 and a shaft 1046, the shaft 1046 extending from the head along the fastener axis 1042. The shaft 1046 is configured to pass through the plate hole 1028 and into the surface 1002. The shaft 1046 may include threads 1048 configured to resist backout of the fastener 1014 from the surface 1002. The head 1044 is configured to enter the plate hole 1028 and abut the inner surface 1030. The fastener 1014 may include, but is not limited to, a nail, a locking screw, and a non-locking screw, such as a compression screw. The head 1044 may include threads 1050 configured to resist backout of the fastener 1014 from the plate hole 1028. The threads 1050 of the head 1044 may correspond to the threads 1032 of the inner surface 1030.

According to one embodiment, the threads 1048 of the shaft 1046 define a different pitch than the threads 1050 of the head 1044, as shown in the illustrated embodiment. According to another embodiment, the threads 1048 of the shaft 1046 define the same pitch as the pitch defined by the threads 1050 of the head 1044.

During insertion of the fastener 1014 to secure the plate 1012 to the surface 1002, alignment of the fastener 1014 and the plate hole 1028 is important. Proper alignment of the fastener 1014 and the plate hole 1028, such that the fastener axis 1042 is aligned, for example is collinear, with the hole axis 1034 improves the quality of the attachment of the plate 1012 and the fastener 1014 and decreases the chances of the fastener 1014 backing out of the plate hole 1028. The fastener guide 1016 is configured to be attached to the plate 1012 and provide a path for the fastener 1014 into the plate hole 1028 such that the fastener axis 1042 and the hole axis 1034 are collinear.

The fastener guide 1016 includes a guide body 1060, and the guide body 1060 includes a plate alignment portion 1062 and a fastener alignment portion 1064. The fastener alignment portion 1064 is configured to receive the fastener 1014 and guide the fastener 1014 toward the plate hole 1028 while maintaining alignment of the fastener axis 1042 and the hole axis 1034. The plate alignment portion 1062 is configured to engage the plate 1012 such that relative movement between the plate 1012 and the fastener guide 1016 is minimized, for example prevented, during passage of the fastener 1014 through the fastener alignment portion 1064 and into the plate hole 1028. The plate 1012 and the fastener guide 1016 define an attached configuration in which a portion of the fastener guide 1016 abuts a portion of the plate 1012. The fastener guide 1016 is configured to be removable from the plate 1012 after the fastener 1014 is secured to the plate 1012.

Referring to FIGS. 15 to 20, the plate alignment portion 1062 includes a base 1066 and a projection 1068 that extends from the base 1066 in a second direction D2. The base 1066 includes a lower surface 1070 that is configured to face the first surface 1022 of the plate body 1020. The projection 1068 includes an inner surface 1072 that is configured to face the side wall 1026 of the plate body 1020. In the attached configuration the lower surface 1070 abuts the first surface 1022, and in the attached configuration the inner surface 1072 abuts the side wall 1026. According to one embodiment, the plate alignment portion 1062 may be flexible such that the lower surface 1070 is able to change shape to correspond to the first surface 1022 of the plate body 1020.

The base 1066 defines a gap 1074 configured to allow passage of the fastener 1014 though the plate alignment portion 1062. According to one embodiment of the disclosure, the gap 1074 is sized so as to allow passage of the fastener 1014 through the plate alignment portion 1062 without interference from the plate alignment portion 1062. The gap 1074 may be at least partially defined by the base 1066. The base 1066 may include a plurality of gaps 1074, a plurality of lower surfaces 1070, or both. Each of the plurality of gaps 1074 is configured to receive the fastener 1014, and each of the plurality of gaps 1074 may be at least partially defined by adjacent ones of the plurality of lower surfaces 1070.

In the attached configuration the base 1066 abuts the first surface 1022 of the plate 1012 such that movement of the fastener guide 1016 relative to the plate 1012 in the second direction D2 is prevented. In the attached configuration the projection 1068 blocks movement of the fastener guide 1016 relative to the plate 1012 in a direction perpendicular to the second direction D2. According to one embodiment of the disclosure, the projection 1068 blocks movement of the fastener guide 1016 relative to the plate 1012 in all directions perpendicular to the second direction D2, or all movement within a plane that is perpendicular to the second direction D2. As shown in the illustrated embodiment, the plate alignment portion 1062 may include a plurality of projections 1068 that each abut a separate location on the side wall 1026 and thus cooperate to block movement of the fastener guide 1016 relative to the plate 1012 in at least one direction perpendicular to the second direction D2.

The projection 1068 may correspond in shape to at least a portion of the side wall 1026 of the plate 1012. Accordingly, the inner surface 1072 may be curved, straight, or partially curved and partially straight. As shown in the illustrated embodiment, the inner surfaces 1072 of a plurality of the projections 1068 may define a portion of a circle that corresponds to a circle defined partially by a portion of the side wall 1026.

The projection 1068 may terminate at a projection lower surface 1076, as shown in the illustrated embodiment. The projection 1068 defines a projection height H2 measured from an intersection of the lower surface 1070 and the projection 1068 to the projection lower surface 1076 along the second direction D2. According to one embodiment of the disclosure, the projection height H2 is substantially equal to the plate height H1. According to another embodiment of the disclosure, the projection height H2 is less than the plate height H1.

The fastener alignment portion 1064 includes an alignment chamber 1078 that extends from the plate alignment portion 1062 in a direction opposite the second direction D2. The alignment chamber 1078 includes a housing 1080, which terminates at an upper surface 1082 of the housing 1080, with respect to the direction opposite the second direction D2. The alignment chamber 1078 may include a chamber axis 1084 that the housing 1080 extends along in the direction opposite the second direction D2. As shown in the illustrated embodiment, the fastener alignment portion 1064 may be elongate along the chamber axis 1084.

The housing 1080 includes a housing inner surface 1086 that faces the chamber axis 1084. The housing inner surface 1086 at least partially defines a through hole 1088 of the alignment chamber 1078. The through hole 1088 is configured to provide a pathway for the fastener 1014 to pass through the alignment chamber 1078, through the gap 1074, and into the plate hole 1028. The through hole 1088 may be further configured to provide a pathway for the fastener 1014 to be removed from the alignment chamber 1078 by moving along the chamber axis 1084 away from the plate hole 1028. The housing 1080 further includes a housing outer surface 1090 that is opposite the housing inner surface 1086 with respect to a radial direction, which includes all directions perpendicular to the chamber axis 1084. According to one aspect of the disclosure, at least a portion of the housing outer surface 1090 corresponds in shape to the side wall 1026. At least a portion of the housing outer surface 1090 and at least a portion of the side wall 1026 may be convex, and a portion of the convex portions of the housing outer surface 1090 and the side wall 1026 may have similar, for example the same, radii of curvature.

The alignment chamber 1078 may include an alignment mechanism 1100 configured to align the fastener axis 1042 with the chamber axis 1084 during movement of the fastener 1014 through the alignment chamber 1078. The alignment mechanism 1100 may be supported by, for example integral with, the housing 1080. According to one aspect of the disclosure, the alignment mechanism 1100 includes a biasing member 1102 that is configured to exert a force on the fastener 1014, the force including a component that is both in a direction perpendicular to the chamber axis 1084 and toward the chamber axis 1084.

As shown in the illustrated embodiment, the biasing member 1102 may include a flexible finger 1104, the flexible finger 1104 including a proximal end 1106 attached to, for example integral with, the housing 1080, and a distal end 1108 spaced from the proximal end 1106 in the second direction D2. According to one embodiment, the distal end 1108 is a free end such that the distal end 1108 is devoid of any direct attachment to the housing 1080. The proximal end 1106 defines a first radial thickness measured radially with respect to the chamber axis 1084, and the distal end 1108 defines a second radial thickness measured radially with respect to the chamber axis 1084. According to one aspect of the disclosure, the second radial thickness may be greater than the first radial thickness.

As shown in the illustrated embodiment, the alignment chamber 1078 may include a gap 1110 that separates the distal end 1108 from the housing 1080. According to another embodiment, the distal end 1108 may be attached to the housing 1080, to the plate alignment portion 1062, or to both. The alignment chamber 1078 may include a pair of gaps 1110 on either side of the biasing member 1102, enabling the biasing member 1102 to move relative to the housing 1080. Alternatively, the alignment chamber 1078 may be devoid of any of the gaps 1110. The alignment chamber 1078 may be constructed from a deformable material, for example an elastically deformable material.

The flexible finger 1104 defines an unbiased state in which there are no forces being applied to the flexible finger 1104, for example by the fastener 1014 being inserted through the alignment chamber 1078, by a user of the kit, etc. When the flexible finger 1104 is in the unbiased state, the flexible finger 1104 is in an unbiased position which is a first distance from the chamber axis 1084. The flexible finger 1104 defines a biased state in which there is at least one force being applied to the flexible finger, for example by the fastener 1014 being inserted through the housing 1080, by a user of the kit, etc. When the flexible finger 1104 is in the biased state, the flexible finger 1104 is in a biased position which is a second distance from the chamber axis 1084, and the second distance is greater than the first distance.

The fastener alignment portion 1064, according to one embodiment, is configured such that the flexible finger 1104 is biased to the unbiased state. Thus the flexible finger 1104 may be configured to move in a radially outward direction with respect to the chamber axis 1084, for example in response to passage of the fastener 1014 through the alignment chamber 1078, and thereby exert the force on the fastener 1014. The alignment mechanism 1100 is configured such that the force is sufficient to align the fastener axis 1042 with the chamber axis 1084 and maintain that alignment during passage of the fastener 1014 through the alignment chamber 1078. The alignment chamber 1078 may be configured such that the fastener 1014 is visible, or at least partially visible, within the through hole 1088. According to one embodiment, at least a portion of the alignment chamber 1078, for example the housing 1080, may include a transparent or translucent material. According to one embodiment, at least a portion of the alignment chamber 1078, for example the housing 1080 may define an opening, for example a slit or cutout, that allows visibility of the interior of the through hole 1088 and the fastener 1014 when the fastener 1014 is positioned within the through hole 1088.

The alignment mechanism 1100 may include a plurality of the biasing members 1102, for example a plurality of the flexible fingers 1104. As shown in the illustrated embodiment, the alignment mechanism 1100 may include a first flexible finger 1104 and a second flexible finger 1104. The alignment mechanism 1100 may be configured such that the first and second flexible fingers 1104 apply equal and opposite forces to the fastener 1014. According to another embodiment, the plurality of biasing members 1102 may include more than two of the biasing members 1102, and the alignment mechanism 1100 may be configured such that a summation of the forces applied by the plurality of biasing members 1102 to the fastener 1014 is zero. Each of the plurality of biasing members 1102 may be spaced equidistantly about the chamber axis 1084.

Referring to FIGS. 20 to 25, a method of securing a plate, such as the plate 1012 to a surface, such as the surface 1002, includes any combination of the steps described below. Attaching the fastener guide 1016 to the plate 1012 such that at least a portion of the projection 1068 faces at least a portion of the side wall 1026 and such that at least a portion of the lower surface 1070 faces the first surface 1022. According to one embodiment, the kit 1010 may include the fastener guide 1016 already attached to the plate 1012, thus eliminating the need for the attaching step to be performed by a user of the kit 1010.

The method may further include the step of attaching the fastener guide 1016 to the plate 1012 such that the chamber axis 1084 is aligned, for example collinear, with the hole axis 1034. As shown in the illustrated embodiment, after attaching the fastener guide 1016 to the plate 1012, the fastener guide 1016 and the plate 1012 are in the attached configuration. In the attached configuration the aligned chamber axis 1084 and the hole axis 1034 may be parallel to the first direction D1. According to another embodiment, in the attached configuration the aligned chamber axis 1084 and the hole axis 1034 may be non-parallel to the first direction D1.

The method may further include the step of moving the fastener 1014 into the through hole 1088 and advancing the fastener 1014 along the chamber axis 1084 toward the plate hole 1028. The advancing step may include the step of rotating the fastener 1014 about the fastener axis 1042 while maintaining alignment of the fastener axis 1042 with both the chamber axis 1084 and the hole axis 1034. According to another embodiment, the kit 1010 may include the fastener 1014 pre-loaded, or positioned within the through hole 1088. According to another embodiment, the kit 1010 may include the fastener 1014 pre-loaded, or positioned within the through hole 1088, the fastener guide 1016 attached to the plate 1012, and the plate 1012, the attached fastener guide 1016, and the pre-loaded fastener 1014 all positioned within a sterile enclosure. The method may further include the step of moving the fastener 1014 out of the through hole 1088 by advancing the fastener 1014 along the chamber axis 1084 away from the plate hole 1028.

The fastener 1014 may be positioned within the through hole 1088 such that contact between the fastener 1014 and the alignment chamber 1078 restricts movement of the fastener 1014 out of the through hole 1088 in a direction opposite the second direction D2. According to one embodiment the contact between the fastener 1014 and the alignment chamber 1078 is sufficient to restrict movement of the fastener 1014 out of the through hole 1088 in a direction opposite the second direction D2 in response to the force of gravity acting on the fastener 1014, for example if the fastener guide 1016 is manipulated such that the upper surface 1082 points toward the ground.

The advancing step may further include the step of abutting the fastener 1014 with the alignment chamber 1078. The abutting step may include abutting the head 1044 with the inner surface 1072, abutting the shaft 1046 with the alignment mechanism 1100, abutting the head 1044 with the alignment mechanism 1100, or any combination thereof. According to one aspect of the disclosure the alignment chamber 1078 is configured to provide an unobstructed path for the fastener 1014 through the through hole 1088 in the second direction D2 until the shaft 1046, for example the threads 1048 engage the alignment mechanism 1100.

The method may further include, after the step of abutting the shaft 1046 with the alignment mechanism 1100, further advancing the fastener 1014 in the second direction D2 toward the plate hole 1028. The step of further advancing the fastener 1014 in the second direction D2 toward the plate hole 1028 includes the step of increasing a distance between first and second ones of the flexible fingers 1104, the distance measured in a plane perpendicular to the chamber axis 1084.

According to an embodiment of the disclosure, the biasing member 1102 may include an extension 1112 that extends from the flexible finger 1104 toward the chamber axis 1084 and terminates at an abutment surface 1114 that at least partially faces the chamber axis 1084. The abutment surface 1114 may be smooth, textured, treaded, grooved, toothed, or any combination thereof. The abutment surface 1114 may flat, curved, for example concave, or partially flat and partially curved. According to one embodiment, the biasing member 1102 may be configured such that as the shaft 1046 abuts the abutment surface 1114, threads are formed in the abutment surface 1114 that correspond to the threads 1048 of the shaft 1046. According to another embodiment, the abutment surface 1114 is preformed with threads that correspond to the threads 1048 of the shaft 1046 prior to the fastener 1014 abutting the abutment surface 1114. As shown in the illustrated embodiment, the extension 1112 is supported by, for example is integral with, the distal end 1108.

As shown in FIGS. 21 and 22, when the flexible fingers 1104 are in the unbiased state the alignment chamber 1078 defines a first distance J1 measured from the abutment surface 1114 of one of the flexible fingers 1104 to the abutment surface 1114 of another of the flexible fingers 1104 in a third direction D3 that is perpendicular to the second direction D2. The kit 1010 is configured such that the first distance J1 is less than a major diameter M1 of the shaft 1046 of the fastener 1014 when the flexible fingers 1104 are in the unbiased state. The kit 1010 may further be configured such that the alignment chamber 1078 defines a second distance J2 measured from the inner surface 1072 of the housing 1080 at a first location to the inner surface 1072 at a second location along the third direction D3. The second distance J2 may be greater than the major diameter M1 of the fastener 1014 as shown in the illustrated embodiment. The alignment chamber 1078 may further be configured such that the second distance J2 is greater than a maximum outer diameter M2, for example defined by the widest part of the head 1044, of the fastener 1014.

The distances described herein may alternatively be measured from a reference surface to an axis rather than to another surface. For example, the first distance J1 may be measured from the abutment surface 1114 of one of the flexible fingers to the chamber axis 1084, the major diameter M1 of the shaft 1046 may be measured from the threaded shaft to the fastener axis 1042, and the first distance J1 is less than the major diameter M1 when the flexible fingers 1104 are in the unbiased state.

Figure 23:
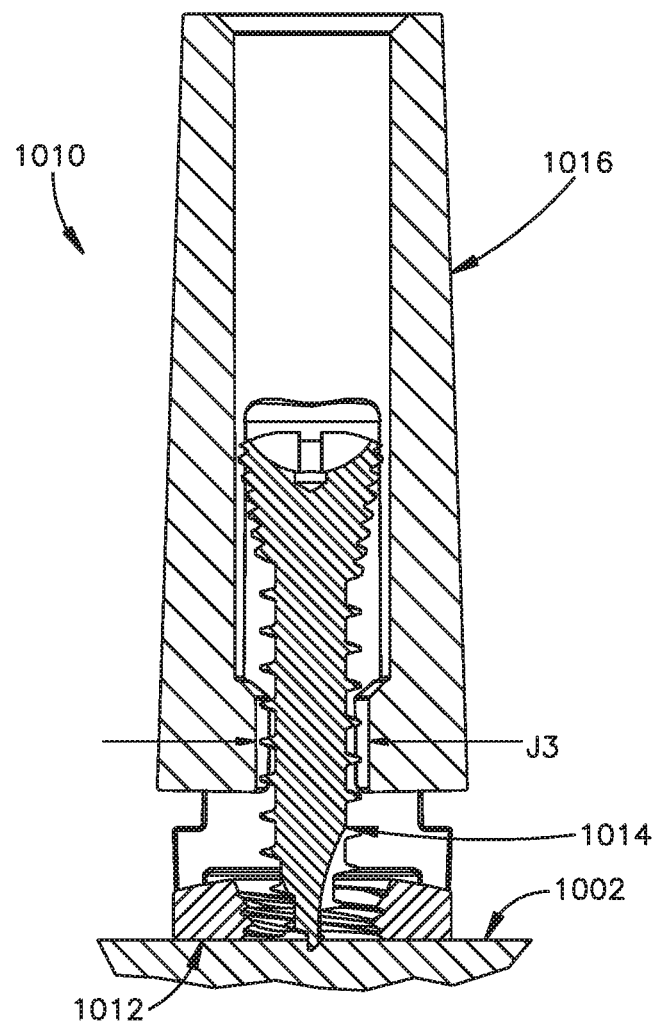
FIG. 23 is a cross-sectional view of the portion of the fastener guide, the portion of the bone plate, and the fastener illustrated in FIG. 21, the fastener guide and the bone plate in the attached configuration, and the fastener in a third position.

As shown in FIG. 23, as the shaft 1046 is advanced between the flexible fingers 1104, the shaft 1046 abuts the abutment surfaces 1114, moving the abutment surfaces 1114 away from each other such that the flexible fingers 1104 are in the biased state and the alignment chamber 1078 defines a third distance J3 measured from the abutment surface 1114 of one of the flexible fingers 1104 to the abutment surface 1114 of another of the flexible fingers 1104 in the third direction D3. The third distance J3 is equal to or larger than the major diameter M1 of the fastener 1014 such that the fastener 1014 is able to advance between the flexible fingers 1104 in the second direction D2.

The method may include the step of applying a force to the fastener 1014, the force configured to maintain alignment of the fastener axis 1042, the chamber axis 1084, and the hole axis 1034 during the step of further advancing the fastener 1014 in the second direction D2 toward the plate hole 1028. As shown in the illustrated embodiment, the force may be applied to the fastener 1014, for example the shaft 1046 or the head 1044, at a location spaced from an entirety of the plate 1012 in a direction opposite the first direction D1, and the force is applied by the flexible fingers 1104.

Figures 24, 25:
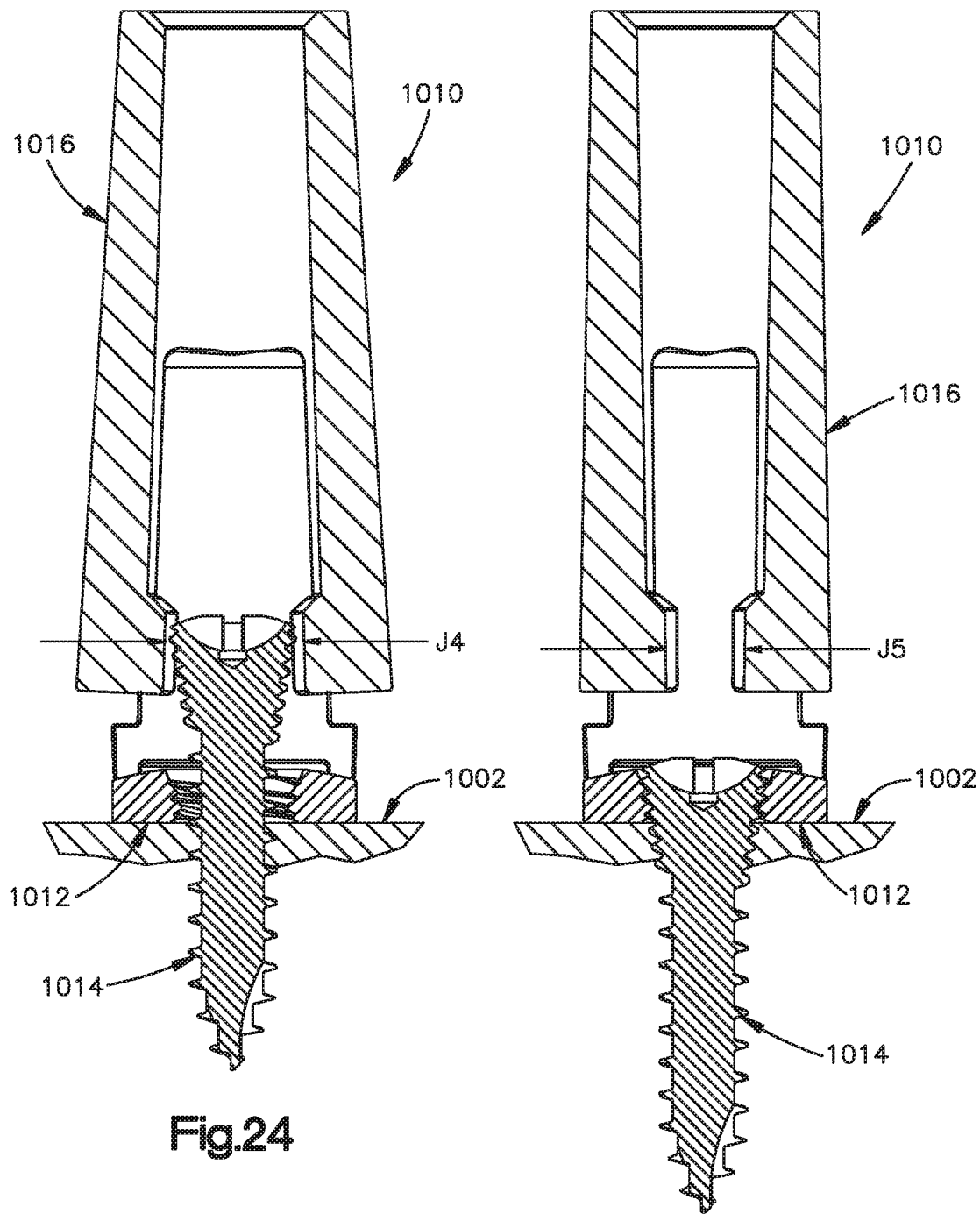
FIG. 24 is a cross-sectional view of the portion of the fastener guide, the portion of the bone plate, and the fastener illustrated in FIG. 21, the fastener guide and the bone plate in the attached configuration, and the fastener in a fourth position.
FIG. 25 is a cross-sectional view of the portion of the fastener guide, the portion of the bone plate, and the fastener illustrated in FIG. 21, the fastener guide and the bone plate in the attached configuration, and the fastener in a fifth position.

As shown in FIG. 24, the method may include abutting the head 1044 with the alignment chamber 1078. The advancing step may include abutting the head 1044 with the biasing members 1102, with the housing inner surface 1086, or both. As shown in the illustrated embodiment, when the head 1044 abuts the abutment surfaces 1114 of the flexible fingers 1104 the alignment chamber 1078 defines a fourth distance J4 measured from the abutment surface 1114 of one of the flexible fingers 1104 to the abutment surface 1114 of another of the flexible fingers 1104 in the third direction D3. The fourth distance J4 is greater than the third distance J3, and greater than or equal to the maximum outer diameter M2.

As shown in FIG. 25, the method may include the step of advancing the fastener 1014 in the second direction D2 until the head 1044 is no longer in contact with the alignment mechanism 1100, for example when the head 1044 abuts the inner surface 1030 of the plate hole 1028. Once an entirety of the fastener 1014 is spaced from the alignment mechanism 1100 in the second direction D2, the alignment chamber 1078 once again is in the unbiased state such that the alignment chamber 1078 defines a fifth distance measured from the abutment surface 1114 of one of the flexible fingers 1104 to the abutment surface 1114 of another of the flexible fingers 1104 in the third direction D3. The fifth distance J5 is less than the fourth distance J4. According to one embodiment, the fifth distance J5 is equal to the first distance J1.

The method may further include securing the fastener 1014 to the plate 1012, for example by mating corresponding threads 1032 and 50, with the fastener axis 1042 and the hole axis 1034 aligned. Once the fastener 1014 is secured to the plate 1012, any combination of the steps listed above may be repeated with additional ones of the fasteners 1014 being inserted through additional ones of the alignment chambers 1078, and into additional ones of the plate holes 1028. The method may further include, after the securing step, the step of removing the fastener guide 1016 from the plate 1012, in a direction opposite the second direction D2. The fastener guide 1016 may then be disposed of, or sterilized for use with another plate 1012.

Referring still to FIGS. 20 to 25, the alignment chamber 1078 may include a proximal portion 120 that includes the upper surface 1082, and a distal portion 122 that includes the alignment mechanism 1100. The distal portion 122 is positioned between the proximal portion 120 and the plate alignment portion 1062 with respect to the second direction D2. The guide body 1060 may configured such that the distal portion 122 expands radially with respect to the chamber axis 1084 during passage of the fastener 1014 through the through hole 1088, while both the proximal portion 120 and the plate alignment portion 1062 do not expand radially with respect to the chamber axis 1084 during passage of the fastener 1014 through the through hole 1088.

Figure 26:
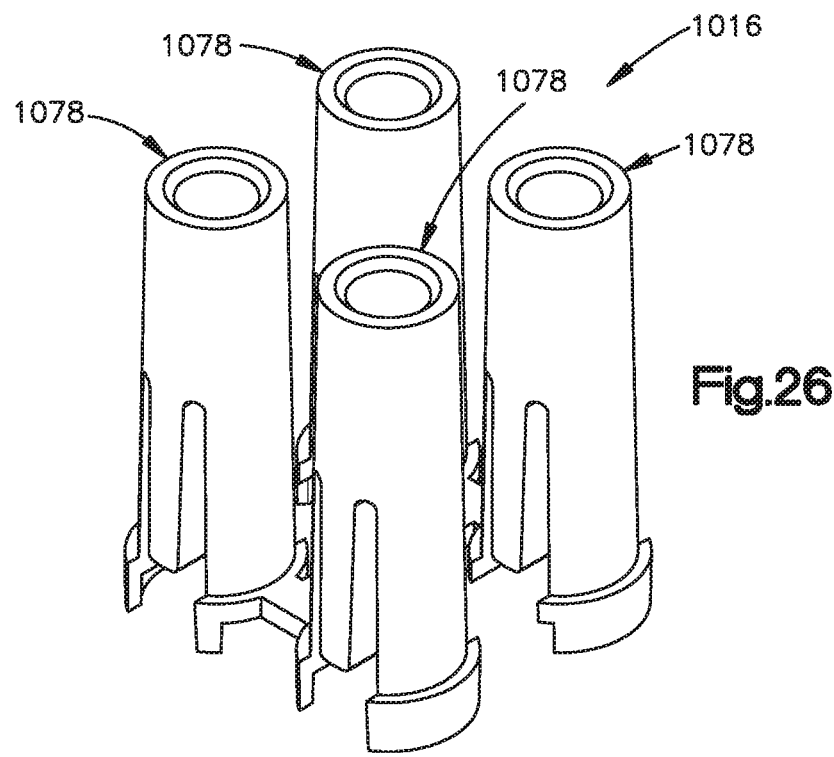
FIG. 26 is an isometric view of the fastener guide according to another aspect of the disclosure.
Figure 27:
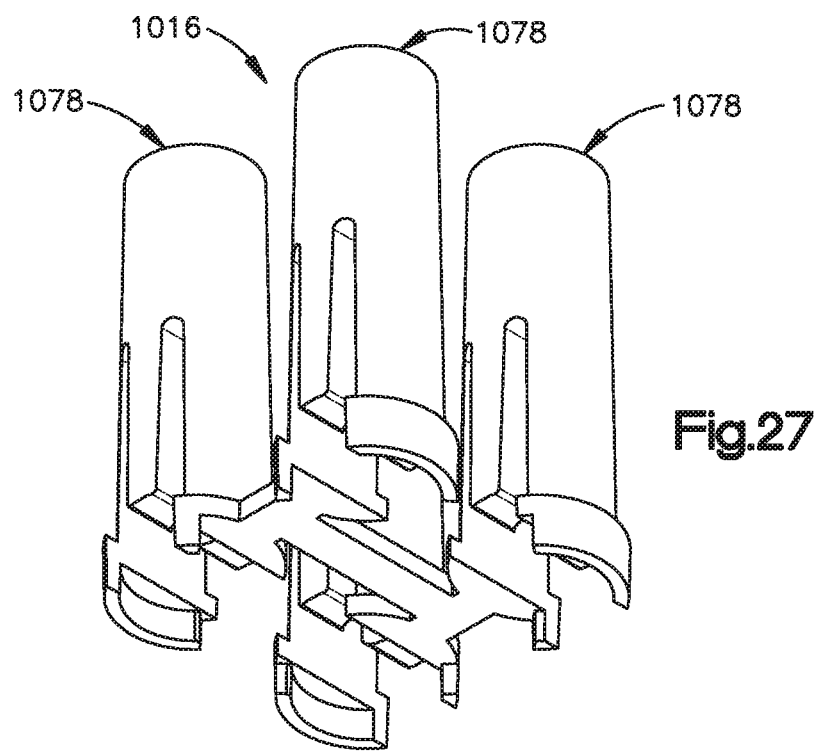
FIG. 27 is another isometric view of the fastener guide illustrated in FIG. 26.
Figure 28:
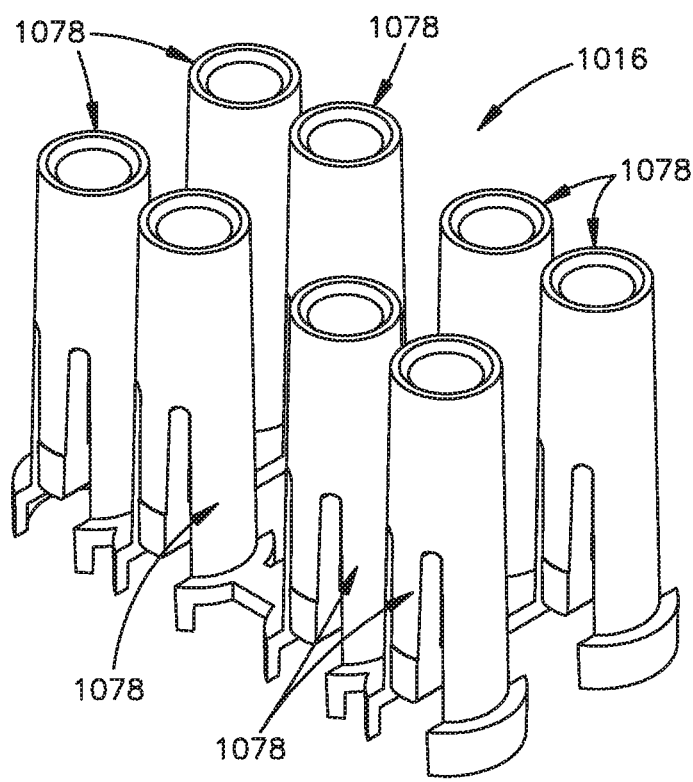
FIG. 28 is an isometric view of the fastener guide according to another aspect of the disclosure.
Figure 29:
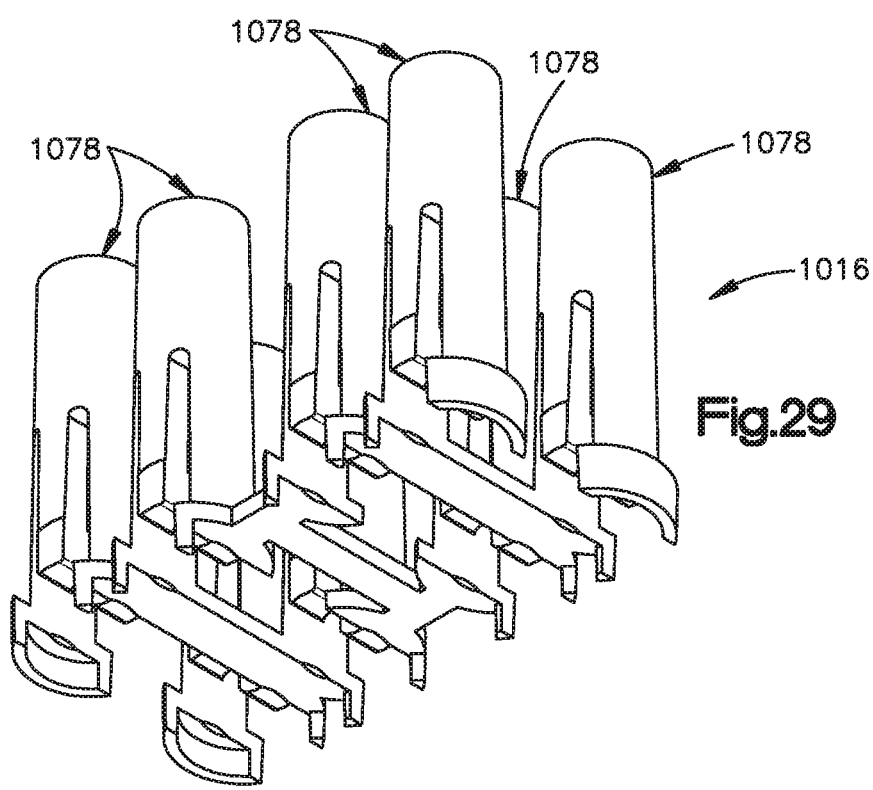
FIG. 29 is another isometric view of the fastener guide illustrated in FIG. 28.

Referring to FIGS. 12 to 29, the fastener guide 1016 may be configured to include a plurality of alignment chambers 1078. The fastener guide 1016 may include a plurality of alignment chambers 1078 aligned in a direction perpendicular to the second direction D2. For example, as shown in FIGS. 12 to 20, the fastener guide 1016 may include alignment chambers 1078 arranged in a 4 by 1 layout. According to another embodiment, the fastener guide 1016 includes a plurality of alignment chambers 1078 arranged in a regular pattern of rows and columns. As shown in FIGS. 26 and 27, the fastener guide 1016 may include alignment chambers 1078 arranged in a 2 by 2 layout. As shown in FIGS. 28 and 29, the fastener guide 1016 may include alignment chambers 1078 arranged in a 4 by 2 layout. According to another embodiment, the fastener guide 1016 includes a plurality of alignment chambers 1078 arranged in a non-regular pattern, which includes any arrangement of alignment chambers 1078 that is not a regular pattern. According to one aspect of the disclosure, the fastener guide 1016 may be configured such that the chamber axis 1084 of each of the plurality of alignment chambers 1078 are parallel to one another. According to another aspect of the disclosure, the fastener guide 1016 may be configured such that the chamber axis 1084 of at least one of the plurality of alignment chambers 1078 is non-parallel with respect to the chamber axis 1084 of another of the plurality of alignment chambers 1078.

According to one embodiment of the disclosure, the kit 1010 includes one or more plates 1012, each of the plates 1012 having an arrangement of plate holes 1028. The kit 1010 further includes one or more fastener guides 1016, each of the one or more fastener guide 1016 including alignment chambers 1078 arranged to match the arrangement of plate holes 1028 of at least one of the one or more plates 1012.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated. All methods described herein can be performed in any suitable order unless otherwise indicated herein or otherwise clearly contradicted by context.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

We claim:

1. A fastener guide configured to align a fastener and a bone plate, the fastener guide comprising:
   a plate alignment portion including a base and a projection that extends from the base in a first direction, wherein the base defines a lower surface that faces the first direction and is configured to abut the bone plate, and the projection extends to a location offset from the lower surface in the first direction; and
   a fastener alignment portion including an alignment chamber, the alignment chamber including a housing and a through hole configured to receive the fastener, the housing extending from the plate alignment portion along a chamber axis in a first direction, and the alignment chamber further including a flexible finger supported by the housing and having an abutment surface that faces the chamber axis and an outer surface that is opposite the abutment surface and is an outermost surface of the fastener guide when the flexible finger is in an undeflected position, wherein the flexible finger extends in the first direction to a free distal end, wherein the flexible finger defines a distance measured from the abutment surface to the chamber axis along a second direction, which is perpendicular to the first direction, and the flexible finger is configured to flex such that the distance increases as the fastener contacts the abutment surface.

2. The fastener guide of claim 1, wherein the flexible finger includes a proximal end and a distal end, the proximal end is attached to the housing, and the flexible finger extends from the housing in a distal direction such that the flexible finger terminates at the distal end.

3. The fastener guide of claim 2, wherein the distal end is a free end that is movable radially with respect to the chamber axis, the distal end includes the abutment surface, and the free end terminates at a location offset from the lower surface in a second direction that is opposite the first direction.

4. The fastener guide of claim 2, wherein the proximal end defines a first radial thickness measured radially with respect to the chamber axis, the distal end defines a second radial thickness measured radially with respect to the chamber axis, and the second radial thickness is greater than the first radial thickness.

5. The fastener guide of claim 1, wherein the flexible finger is a first flexible finger, the abutment surface is a first abutment surface, and the fastener guide further comprises a second flexible finger, and the second flexible finger includes a second abutment surface, wherein a distance is defined from the second abutment surface to the chamber axis along the second direction, and the second finger is flexible such that the distance from the second abutment surface to the chamber axis is configured to increase as the fastener contacts the second abutment surface.

6. The fastener guide of claim 5, wherein the flexible finger is configured such that the first flexible finger and the second flexible finger are each configured to flex away from each other as the fastener contacts the abutment surface.

7. The fastener guide of claim 1, wherein the projection includes an inner surface that is substantially perpendicular to the lower surface, and the fastener guide is configured to be attached to the bone plate such that the inner surface faces the bone plate.

8. A kit configured to repair a defect in a surface, the kit comprising:
   the fastener guide of claim 1;
   the bone plate including a first surface, a second surface opposite the first surface, a side wall that extends between the first surface and the second surface thereby defining an outer perimeter of the bone plate, a plate hole that extends through both the first surface and the second surface along a hole axis, and an inner surface that extends between the first surface and the second surface and that defines the plate hole; and
   the fastener including a head and a shaft, the shaft extends from the head, and the shaft is configured to be inserted through the plate hole and into the surface to secure the bone plate to the surface,
   wherein the fastener guide is configured to be attached to the bone plate such that: 1) the lower surface of the base abuts the first surface of the bone plate, 2) an inner surface of the projection abuts the side wall of the bone plate, and 3) the hole axis is collinear with the chamber axis.

9. The kit of claim 8, wherein the fastener guide is configured to be attached to the bone plate such that: 1) movement of the fastener guide relative to the bone plate in the first direction is blocked by interference of the lower surface of the base and the first surface of the bone plate, and 2) movement of the fastener guide in a direction perpendicular to the first direction is resisted by interference of an inner surface of the projection and the side wall of the bone plate.

10. The kit of claim 8, wherein the second surface of the bone plate is configured to face the first surface, the second surface is spaced from the first surface in a third direction, the bone plate defines a maximum plate height measured from the first surface to the second surface in the third direction, the projection includes a projection lower surface at which the projection terminates with respect to the first direction, the projection defines a projection height measured from an intersection of the lower surface and the projection to the projection lower surface along the first direction, and the maximum plate height is greater than the projection height.

11. The kit of claim 8, wherein a first diameter of the through hole measured at a first location on the alignment chamber is greater than a second diameter of the through hole measured at a second location on the alignment chamber, and the first location is spaced from the second location in the second direction.

12. The kit of claim 11, wherein the alignment chamber includes a first flexible finger having a first abutment surface that faces the chamber axis, and the second location is on the first abutment surface, the alignment chamber includes a second flexible finger having a second abutment surface that faces the chamber axis, and the second diameter is measured from the first abutment surface to the second abutment surface.

13. The kit of claim 8, wherein the alignment chamber is a first alignment chamber, the through hole is a first through hole, the chamber axis is a first chamber axis and the fastener alignment portion includes a second alignment chamber including a second through hole that both extends along a second chamber axis and is configured to receive the fastener.

14. The kit of claim 13, wherein the inner surface of the bone plate is a first inner surface of the bone plate, the plate hole is a first plate hole, the hole axis is a first hole axis, the bone plate includes a second inner surface that defines a second plate hole that extends through both the first surface and the second surface along a second hole axis, and the fastener guide is configured to be attached to the bone plate such that the second hole axis is collinear with the second chamber axis.

15. The fastener guide of claim 1, further comprising an extension that extends radially from the flexible finger toward the chamber axis, wherein the extension is sized to abut a shaft of the fastener as the fastener is driven through the through hole.

16. The fastener guide of claim 1, wherein the plate alignment portion and the fastener alignment portion define a one-piece structure.

17. A fastener guide configured to align a fastener with a fastener opening of a bone plate, the fastener guide comprising:
 a plate alignment portion including a base and at least one projection that extends from the base, wherein the base defines a lower surface that faces a first direction and is configured to abut the bone plate; and
 an alignment chamber including a housing having an inner surface that, in turn, defines a through hole that extends through the housing along a chamber axis and is sized to receive the fastener, the alignment chamber further including a plurality of flexible fingers that extend from the housing in the first direction and define respective abutment surfaces that face the chamber axis, wherein the fingers terminate in the first direction at respective free ends, and the plate alignment portion and the alignment chamber define a one-piece structure,
 wherein the flexible fingers are resiliently deflectable with respect to the housing from a relaxed position to a deflected position, such that when the flexible fingers are in the relaxed position, the abutment surfaces are offset toward the chamber axis with respect to the inner surface of the alignment housing, and the abutment surfaces move away from the chamber axis when the flexible fingers deflect from the relaxed position to the deflected position,
 wherein the free ends are offset from the lower surface in a second direction that is opposite the first direction.

18. The fastener guide of claim 17, wherein the one-piece structure further comprises a plurality of the alignment chambers, wherein the at least one projection is configured to couple to the bone plate so as to align the through hole of each of the plurality of alignment chambers with respective different fastener openings of the bone plate.

* * * * *